US011911717B2

(12) United States Patent
Arthur et al.

(10) Patent No.: US 11,911,717 B2
(45) Date of Patent: Feb. 27, 2024

(54) METHOD AND APPARATUS FOR APPLYING AGGREGATING SAMPLING

(71) Applicants: FREMONTA Corporation, San Jose, CA (US); The United States of America as Represented by the Secretary of Agriculture, Washington, DC (US)

(72) Inventors: Terrance Arthur, Hastings, NE (US); Tommy Wheeler, Clay Center, NE (US); Eric Child Wilhelmsen, Milpitas, CA (US); Florence Q. Wu, Milpitas, CA (US); Yongqing Huang, Newark, CA (US); Wei Wu, Fremont, CA (US)

(73) Assignee: Fremonta Corporation, San Jose, CA (US)

( * ) Notice: Subject to any disclaimer, the term of this patent is extended or adjusted under 35 U.S.C. 154(b) by 900 days.

(21) Appl. No.: 16/525,350

(22) Filed: Jul. 29, 2019

(65) Prior Publication Data

US 2020/0030722 A1 Jan. 30, 2020

Related U.S. Application Data

(60) Provisional application No. 62/711,167, filed on Jul. 27, 2018.

(51) Int. Cl.
*G01N 33/02* (2006.01)
*B01D 21/26* (2006.01)
(Continued)

(52) U.S. Cl.
CPC ......... *B01D 21/262* (2013.01); *C12Q 1/6888* (2013.01); *G01N 1/02* (2013.01);
(Continued)

(58) Field of Classification Search
CPC .... G01N 1/02; G01N 1/405; G01N 2001/022; G01N 2001/028; G01N 33/02; G01N 33/12
See application file for complete search history.

(56) References Cited

U.S. PATENT DOCUMENTS 5,868,928 A    2/1999 Bradley et al.
2001/0017755 A1  12/2001 Lichte et al.
(Continued)

FOREIGN PATENT DOCUMENTS

CN    102296103    12/2011
CN    205880240 U   1/2017
(Continued)

OTHER PUBLICATIONS

International Search Report and Written Opinion in PCT/US19/43991, dated Dec. 6, 2019.
(Continued)

*Primary Examiner* — Natalie Huls
(74) *Attorney, Agent, or Firm* — Kilpatrick Townsend & Stockton LLP

(57) ABSTRACT

Certain aspects of the present disclosure relate to methods and apparatus for microbial sampling of foods. For example, a method may include providing at least one aggregating sampler at one or more sampling locations, and sampling a production lot of produce or other food items such as meat using the at least one aggregating sampler to create one or more samples that makes up a microbial sampling. Certain aspects of the present disclosure relate to methods and apparatus for microbial sampling of foods. For example, an apparatus, such as a microbial aggregating sampler, may include a covering having a microbial sampling material with a pocket formed in the covering to receive an appendage or a tool for handling of the covering.

31 Claims, 22 Drawing Sheets

(51) Int. Cl.
*C12Q 1/6888* (2018.01)
*G01N 1/02* (2006.01)
*G01N 1/40* (2006.01)
*B01D 61/02* (2006.01)
*B01D 61/14* (2006.01)

(52) U.S. Cl.
CPC ........... *G01N 1/4077* (2013.01); *G01N 33/02* (2013.01); *B01D 61/025* (2013.01); *B01D 61/145* (2013.01); *G01N 2001/4088* (2013.01)

(56) References Cited

U.S. PATENT DOCUMENTS

| | | |
|---|---|---|
| 2001/0047755 A1 | 12/2001 | Lichte et al. |
| 2003/0023149 A1 | 1/2003 | Montemagno et al. |
| 2006/0129327 A1 | 6/2006 | Ikro et al. |
| 2008/0264186 A1* | 10/2008 | Nacson ................... G01N 1/02 73/863.12 |
| 2009/0139828 A1 | 6/2009 | Burstrom et al. |
| 2014/0046722 A1 | 2/2014 | Rosenbloom et al. |
| 2014/0220193 A1* | 8/2014 | Hocker ................... B65G 15/00 374/141 |
| 2014/0345364 A1* | 11/2014 | Lin ..................... G01N 15/0606 73/28.01 |
| 2015/0241401 A1* | 8/2015 | Wu .......................... G01N 1/02 435/309.1 |

FOREIGN PATENT DOCUMENTS

| | | |
|---|---|---|
| CN | 106742583 A | 5/2017 |
| CN | 107020169 A | 8/2017 |
| CN | 206818437 U | 12/2017 |
| CN | 207369990 U | 5/2018 |
| KR | 10-2015-0080036 A | 7/2015 |

OTHER PUBLICATIONS

Ottesen et al. Co-enriching microflora associated with culture based methods to detect *Salmonella* from tomato phyllosphere. PloS one. Sep. 9, 2013;8(9):e73079.

* cited by examiner

300

| Treatment | Average CFU/cm2 |
|---|---|
| Stomached | 292 |
| 1 Contact, Instant | 42 |
| 1 Contact, 30 seconds | 53 |
| 1 Contact, 60 seconds | 51 |
| 2 Contacts, Instant | 138 |
| 4 Contacts, Instant | 218 |

Table 1

FIG. 3

| Treatment | Average CFU/cm2 |
|---|---|
| Stomached | 313 |
| 1 Contact, Instant | 109 |
| 1 Contact, 30 seconds | 92 |
| 1 Contact, 60 seconds | 114 |
| 2 Contacts, Instant | 191 |
| 4 Contacts, Instant | 390 |

Table 2

FIG. 4

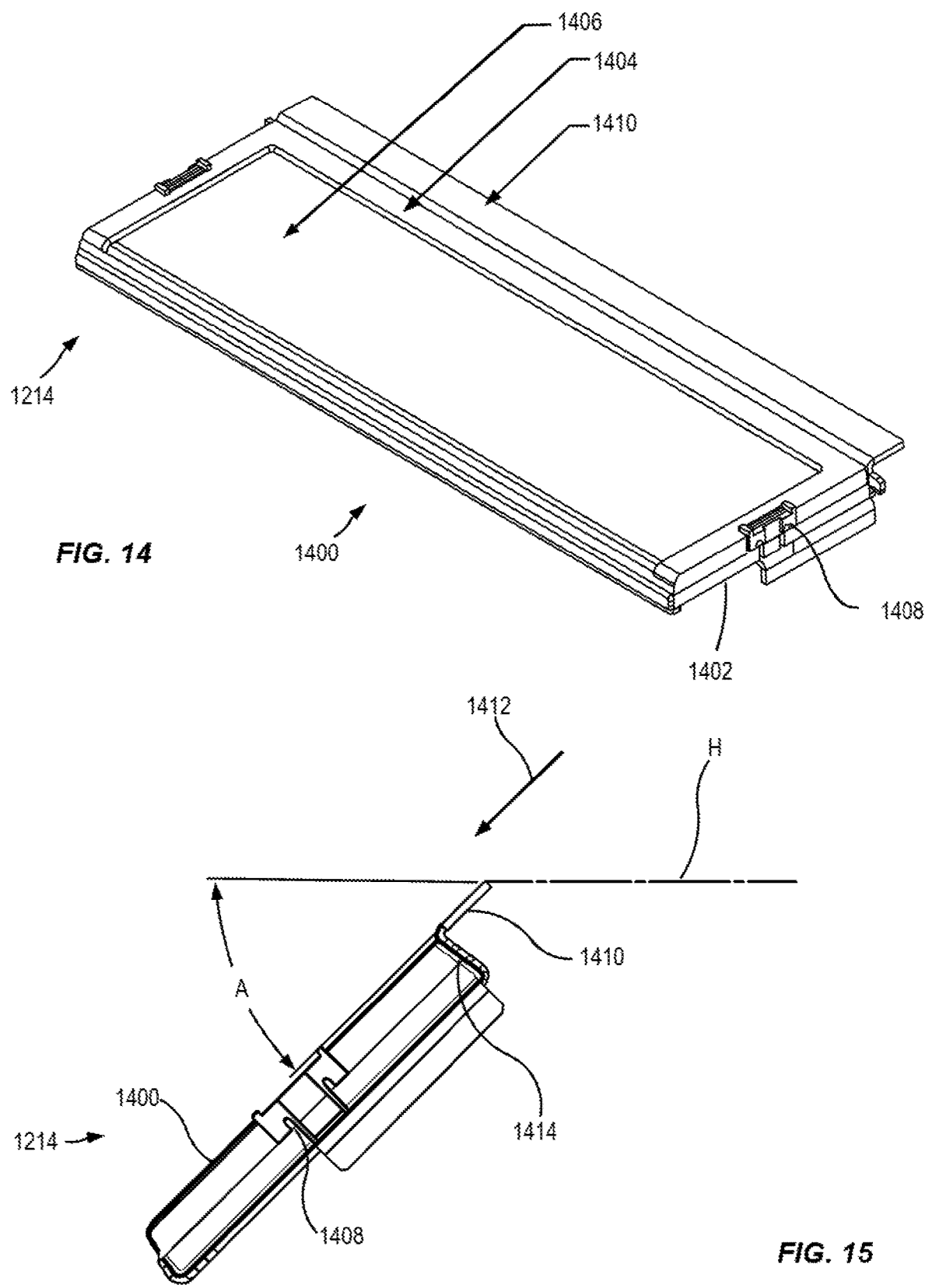

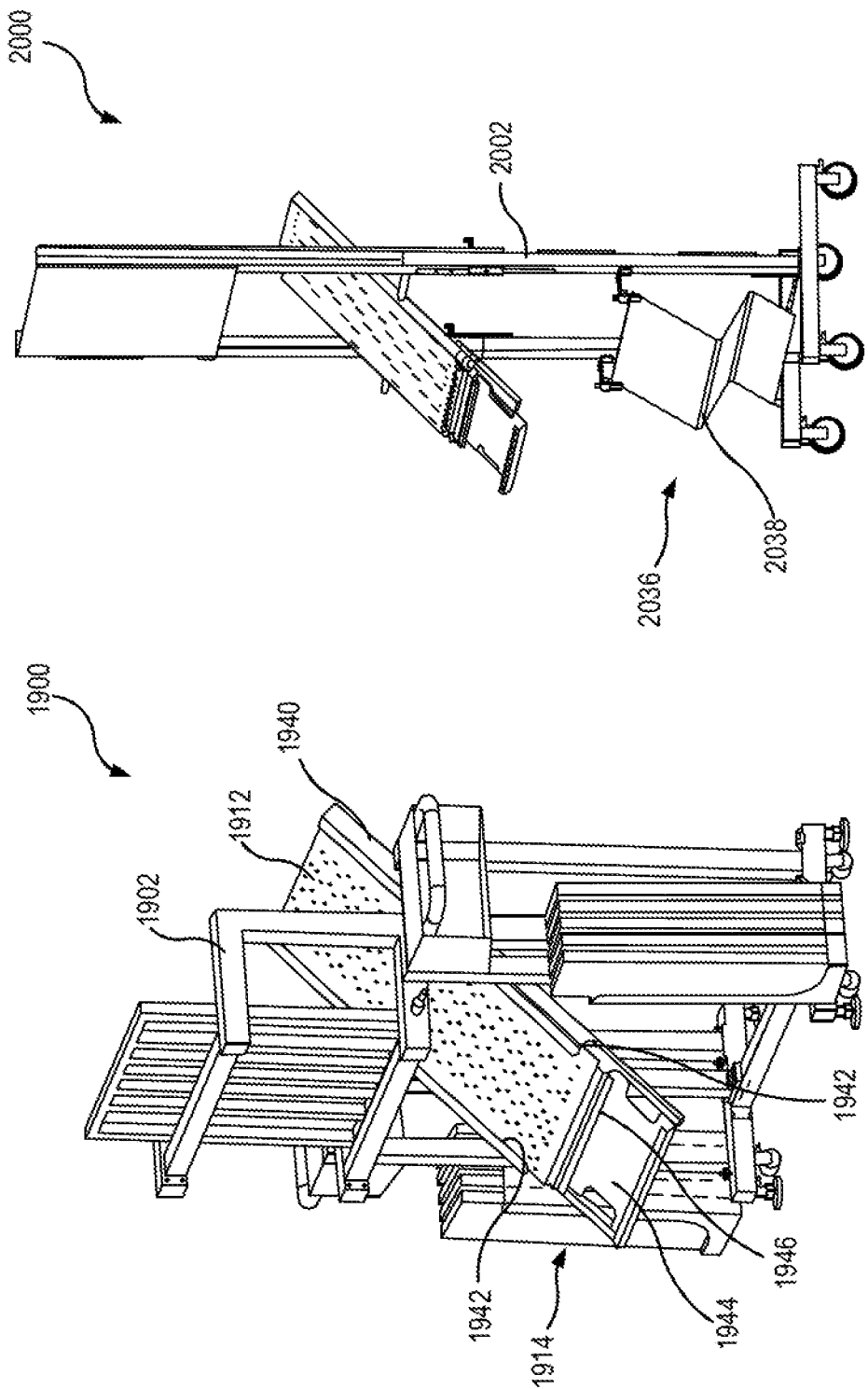

METHOD AND APPARATUS FOR APPLYING AGGREGATING SAMPLING

CROSS-REFERENCES TO RELATED APPLICATIONS

This application claims the benefit of U.S. Provisional Application No. 62/711,167 filed on Jul. 27, 2018, the entire contents of which are incorporated herein by reference.

This application is generally related to the following applications: U.S. Non-Provisional application Ser. No. 14/625,308 filed Feb. 18 2015; and U.S. Non-Provisional application Ser. No. 16/057,137 filed Aug. 7, 2018; the entireties of which are incorporated herein by reference for all purposes.

BACKGROUND

Field of the Disclosure

The present disclosure relates generally to improving the food safety of ready-to-eat produce and other food items and providing process validation, and more particularly, to methods and apparatus for microbial sampling of food items.

Description of Related Art

The microbial testing process has undergone tremendous change in recent years. Traditional plating techniques for enumeration and detection have given way to faster and more specific antibody and molecular biology based techniques. These newer techniques may not require time for colonies to form but they may generally require enrichment culture to collect enough of the target organism and remove interference.

In the ready-to-eat produce industry, millions of dollars are spent collecting grab samples attempting to demonstrate the safety of products in an effort to meet demands by customers for an ever increasing numbers of tests. These efforts may be technically and statistically flawed and may not meet the expectations of assuring food safety. Particularly, grab samples are too small to represent the production lots of material. Production lots of material are too heterogeneous for grab sampling to be descriptive of the production lot. Further, results arrive too slowly to make decisions without sacrificing quality. Pathogens levels are generally so low that the occasional positive sample reflects the background that is always present rather than a deviation from the norm. The ready-to-eat produce industry may benefit from an effective assay of cross contamination and cross contamination control. It may also benefit from an effective measure of process efficacy and deviation in processing. Increasing the effectiveness of raw material testing may help improve food safety practice.

Thus, as the demand for microbial sampling continues to increase, there exists a desire for further improvements in sampling techniques and technology. Preferably, these improvements should be applicable to other related technologies and the methods and devices that employ these technologies.

BRIEF SUMMARY

The systems, methods, and devices of the disclosure each have several aspects, no single one of which is solely responsible for its desirable attributes. Without limiting the scope of this disclosure as expressed by the claims which follow, some features will now be discussed briefly. After considering this discussion, and particularly after reading the section entitled "Detailed Description" one will understand how the features of this disclosure provide advantages that include improved microbial sampling of foods.

Certain aspects provide a method for microbial sampling of foods. The method generally includes gathering a microbial sampling from one or more food items, extracting microorganisms from the microbial sampling, concentrating the microorganisms, cleaning the microorganisms, tallying the relative presence of the microorganisms and any potential pathogens, aggregating this information of the microorganism tally into a microorganism report, confirming the microorganism tally, and reporting the microorganism report of the microorganism tally.

Certain aspects provide a method for microbial sampling of foods. The method generally includes providing at least one aggregating sampler at one or more sampling locations, and sampling, using the at least one aggregating sampler, a production lot of produce creating one or more samples that makes up a microbial sampling.

Aspects generally include methods, apparatus, systems, computer readable mediums, and processing systems, as substantially described herein with reference to and as illustrated by the accompanying drawings.

In one aspect, the invention pertains to aggregating sampling. In some embodiments, the invention includes use of an aggregating sampler. An aggregating sampler for microbial sampling of consumable products, the sampler comprising: a mobile frame; a guide coupled to the mobile frame and having a guide surface positioned such that the consumable products received upon the guide surface pass along the guide surface; and a sample sheet coupled to the guide and/or mobile frame and positioned along or adjacent a lower portion of the guide surface at a non-horizontal angle such that the consumable products received from the guide surface upon the sample surface pass along a sample surface of the sample sheet. In some embodiments, the sample sheet comprises a microbial sampling material to contact the consumable products that pass along the sample surface.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

FIG. 3 illustrates a Table 1 that includes example treatments and results for meat sampling, in accordance with aspects of the present disclosure.

FIG. 4 illustrates a Table 2 that includes example treatments and results for leafy sampling, in accordance with aspects of the present disclosure.

FIG. 14 illustrates a cartridge for use within a mobile aggregating sampler that includes a mobile frame in accordance with aspects of the present disclosure.

FIG. 15 illustrates the cartridge in accordance with aspects of the present disclosure.

FIG. 19 illustrates a mobile aggregating sampler that includes a mobile frame in accordance with aspects of the present disclosure.

FIG. 20 illustrates a mobile aggregating sampler that includes a mobile frame in accordance with aspects of the present disclosure.

To facilitate understanding, identical reference numerals have been used, where possible, to designate identical elements that are common to the figures. It is contemplated that elements disclosed in one aspect may be beneficially utilized on other aspects without specific recitation.

DETAILED DESCRIPTION

Figure 1:
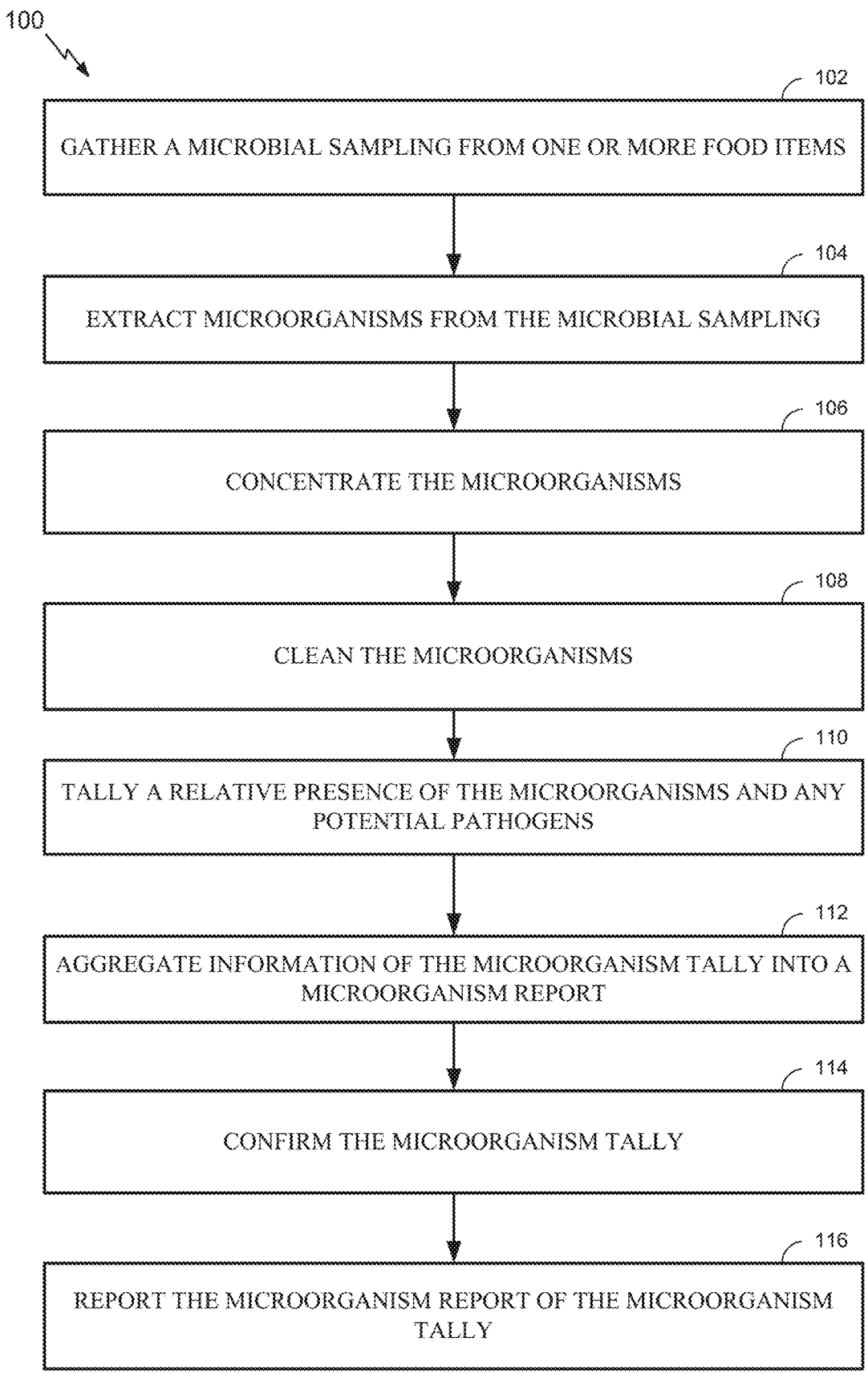
FIG. 1 illustrates example operations for microbial sampling, in accordance with aspects of the present disclosure.

Aspects of the present disclosure provide apparatus, methods, and/or systems for automated and semi-automated microbial sampling of foods.

The following description provides examples, and is not limiting of the scope, applicability, or examples set forth in the claims. Changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim. The word "exemplary" is used herein to mean "serving as an example, instance, or illustration." Any aspect described herein as "exemplary" is not necessarily to be construed as preferred or advantageous over other aspects.

In one embodiment, devices are assembled and linked to a rapid reporting system to provide a more representative sampling and faster analysis of a food product. In another embodiment, a similar system provides for robotically sampling a field crop and delivering results with a mobile laboratory. Both embodiments can include a two-stage screening system for speed and for economy.

There has been little evolution in sampling and sample preparation for submission to these advanced and rapid analytical techniques. One technique is to collect periodic samples or random grabs from a lot. This sample is extracted by homogenization or stomaching and then either a portion analyzed directly when high populations are expected or enriched prior to analysis. Liquid samples and particularly water samples can be filtered to allow analysis of larger samples. For special purposes but generally not for routine analysis, liquid samples can be concentrated by centrifugation to pellet microorganisms. There are statistically based sampling plans as recommended by academics or international organizations, but these sampling plans are rarely practical and mostly cost prohibitive. In use, such sampling plans based on periodic samples or random grabs have a very low data density. Furthermore, these sampling plans intrinsically have sampling biases due to lot geometry where portions of the lot are essentially not sampled and the heterogeneous nature of microorganism distribution.

Some microbial testing assumes that the test organisms are evenly distributed allowing a grab sample to be representative of the whole. This flawed assumption only accounts for inhomogeneous distributions in aggregate. Test and release inspection based on grab samples may be flawed to the extent that grab sampling can inherently miss significant contamination. Furthermore, the size the sample limits the detection limit to levels that may be order of magnitude above the background rate and the level where risk becomes imminent. On the other hand, microbial proliferation during enrichment culture occurs under conditions selected to favor the growth of the potential pathogens which often have no relationship with the commercial conditions of storage and therefore generates extorted perception of microbial growth risk.

One or more embodiments as disclosed herein may address these short comings of the current sampling and testing practice and provides a system to generate more meaningful, real time or near real time, onsite assessment of microbial contamination risk.

Example of Automated and Semi-Automated Microbial Sampling of Foods

In accordance with one or more aspects of embodiments disclosed herein, automated and semi-automated microbial sampling of foods is provided. For example, devices may be assembled and linked to a rapid reporting system to provide a more representative sampling and faster analysis of a food product. In another case, a system may provide robotic sampling of a field crop and may deliver results with a mobile laboratory. Both examples can include a two-stage screening system that allow for increased speed and economy.

In one or more cases, a method and system of microbial sampling includes providing a sampling sheet, such as a MicroTally Sheet, which is then used with a continuous sampling device (CSD) to collect biological agents. The CSD may change the sampling sheet automatically between samples. The sampling sheet is then used for analysis. Particularly, target bacteria may be removed from the sampling medium. The samples of target bacteria are cleaned up and concentrated using a treater and made suitable for analysis. The treated sample is then analyzed using molecular or biochemical methods and target agents are detected with acceptable accuracy and sensitivity. A cloud based data reporting system with user appropriate dashboards to report actionable information and facilitate timely decision making may also be provided. It is appreciated that any of the reporting aspects described herein could be performed by the reporting system automatically so as to provide for faster reporting.

For example, FIG. 1 illustrates specific operations 100 for microbial sampling, in accordance with aspects of the present disclosure.

Specifically, operations 100 begin, at block 102, with gathering a microbial sampling from one or more food items which may include, for example, produce, meat, and other food products. At block 104, operations 100 include extracting microorganisms from the microbial sampling. At block 106, the operations 100 include concentrating the microorganisms. The operations 100, at block 108, include cleaning the microorganisms. Further, the operations 100 include, at block 110, tallying the relative presence of the microorganisms and any potential pathogens. The operations 100 also include, at block 112, aggregating this information of the microorganism tally into a microorganism report. At block 114, the operations include confirming the microorganism tally. The operations may also include, at block 116, reporting the microorganism report of the microorganism tally.

In one or more cases, sampling may include using a sampling sheet or swab that collects a sample and is stomached in a 300 micron partitioned bag with 200 mls of eluting buffer and stomached. Concentration and cleanup of the sample may include siphoning an eluting buffer and entrained organisms through proprietary sequential filter and the targets may be deposited on a 0.22 micron PC filter. The targets are analyzed from the filter which may include for example, DNA purified and qPCR being run for Index elements including pathogen intensity, Enteric status, and/or positive control. Cloud based reporting based on, for example Ignition and SQL database, may be provided with user appropriate dashboards to provide timely actionable information In accordance with one or more cases, pathogens may be confirmed by resampling and enrichment procedures, by resampling and doing definitive pathogen tests, or by doing confirmation tests on the original DNA depending on the regulatory guidance. In one or more cases a cassette and cartridge system may be implemented to streamline the sampling process. Although not required, eliminating the use of a stomacher and partitioned bag may be provided in one or more cases. A binding collector may be provided to replace the PC membrane filter which may help streamline the sample delivery to the detector and potentially eliminate the need for DNA purification. Use of Ribosomal RNA may become a new standard for one or more such cases. In one or more cases, a detector may use flow amplification and laboratory on a chip type technology to further reduce detection times and costs.

To best address all the short comings in current practice numerous improved elements may come together. Taken individually each improvement addresses some of the short comings and yields some advantages. Leaping all the way to a complete solution may beyond the sophistication of some industry classes so intermediate steps are considered for each element. For the initial discussion, the elements under consideration include Sampling, Extraction, Concentration, Cleaning, Screening Detection, Second Stage Sampling of Suspected Lots, Reporting, and Information Roll Up. Although not as desirable, a more conventional enrichment can be used instead of Concentration. Each of these elements is discussed below.

Thus, the timeframe from sampling to information may be driven by the needs of the business class but is not limited thereto. Short shelf-life product can justify greater speed. Valuable commodities such as meat products will want more testing to limit exposure when a problem is expected or anticipated. These factors will impact the degree which a complete automated solution is implemented.

Examples of Sampling

There are practical limits to the amount of product that can be sampled by conventional means. Without heroic efforts samples are limited to small fraction of a pound (generally 150 grams or less but some labs are routinely testing as much as 300 grams) which lead to operating curves for c=0 acceptance that have an inflection at about 1 CFU/pound. The net effect of such sampling and testing is the erroneous belief that the worst lots are detected when 1 positive is found in many hundreds or thousands of samples. Unfortunately, this testing is so far removed from the range of interest; it is little more than a random selection of lots to be rejected.

A manual sheet based sampling can increase the effective sampling weight 20 or 30 fold which is enough to move the operating curve about an order of magnitude to the left to about 0.1 CFU/pound if the same c=0 inspection criteria are used. Similarly, if a continuous sampling method is used, the effective sample can be increased 200 to 300 fold yielding an additional order of magnitude in LOD to about 0.01 CFU/pound.

Either of these approaches has the advantage of being nondestructive and can yield executional efficiencies. However, the real advantage comes when this LOD is traded off for statistical process control with a two-stage acceptance criterion where deviation from normal are detected as opposed to randomly selecting lots for reallocation. This concept is discussed more fully below when this discussion returns to screening detection. This is an important distinction when the goal is to improve the food safety of a product. This line of argument also permits the more rapid detection of many cells rather than waiting for one cell to grow into many cells. With the recognition of the power of the larger and effective sampling procedure, there may be a need to expand the range of tooling to apply this technology to a broader array of products with alternative geometries and increased levels of automation. For example, the geometry can be altered to allow sampling of a powder flow through a pipe with a circular geometry where a pipe segment is exchanged between lots. The pipe section would either be lined with sampling material or better include baffles maximizing product contact with the sampling surfaces. Alternatively, one can envision vertical chutes below pocket fillers to sample product just prior to bagging in a form fill and seal machine.

A microbial sampling may be included, for example, non-woven fabric, various micro fiber materials, sponges, and/or any absorbent sheet material.

Additionally, the utility of these sampling approaches can be increased with automation. A feed cartridge can be used to deliver multiple sheets to the sampling location at one time. This cartridge would be placed on the line after sanitation has completed all preparations protecting the drive mechanisms from the harsh cleaning process.

Similarly, a magazine of cassettes can be loaded to collect individual pieces of sampling material. Both the cartridge and cassette are engineered to advance the sampling material when appropriate, (e.g., when a lot is completed, when a tote is moved, etc.). The motive force to advance sampling sheets can be provided by a motor, or supplied by a manual crank or handle, or by an operator depending on the specifics of the operation. Both cassette and cartridge may be designed to protect the microbial integrity of the contents. The cartridges may prevent microbial growth after sampling, external contamination, and cross contamination between lots.

The sampling material can be mounted on an inert backing material to facilitate the sanitary placement of sampling sheets. Alternatively, sheets of sampling material can be separated by short spaces of inert material to ensure that used sampling materials do not contaminate other sheets.

The usual design parameters for process equipment may be applied to these devices including, for example, an aggregating sampler. For example, heavy gauge 316 stainless is an appropriate material. When the sampling device is not in place, the location may be passive such as a dead plate where product passes without damage or hindrance. It may be sanitary design from the beginning such that it is easily cleaned.

In one case, for this automation to have maximal benefit, the cartridges may carry the information regarding the sample they contain. If the sample is used in a manual mode, an electronic transfer of this information along with the sample is also advantageous to avoid human error and speed the flow of information. This transfer of information can occur through the cloud using barcodes, a database and location information.

Another class of geometries is necessary to extend the power of this sampling to agricultural commodities in the field. Such sampling has utility beyond testing for human pathogens in that it can be used for testing for plant pathogens that can decrease the productivity of a crop. For example, early detection of mildew spores prompt early harvest of a spinach field. Detection of blight in a wheat or corn field might prompt the use of a disease control measure on the affected field before the blight destroys the crop.

Depending on the field crop, an octopus tentacle configuration may be the appropriate geometry where strands of the sampling material are slide across the surface of the crop. These strands can be fuzzy cords or strips of material depending on what provide the greatest effective contact. These tentacles can be contacted to the crop by various mechanisms including robots, tractors, hand carrying or drones. It is most important that the altitude be held constant to allow contact while minimizing damage to the crop. To increase the effectiveness of the sampling, it can be advantageous to wick moisture down these tentacles or install vacuuming or sucking mechanism.

For crops that present a more uniform top surface such as baby greens or spinach, sheet materials can be more effective as new upturned leave surfaces are missed. For these crops, air based sampling with suction or electrostatics that increases microbial sampling efficiency presents an interesting alternative.

Figure 2:
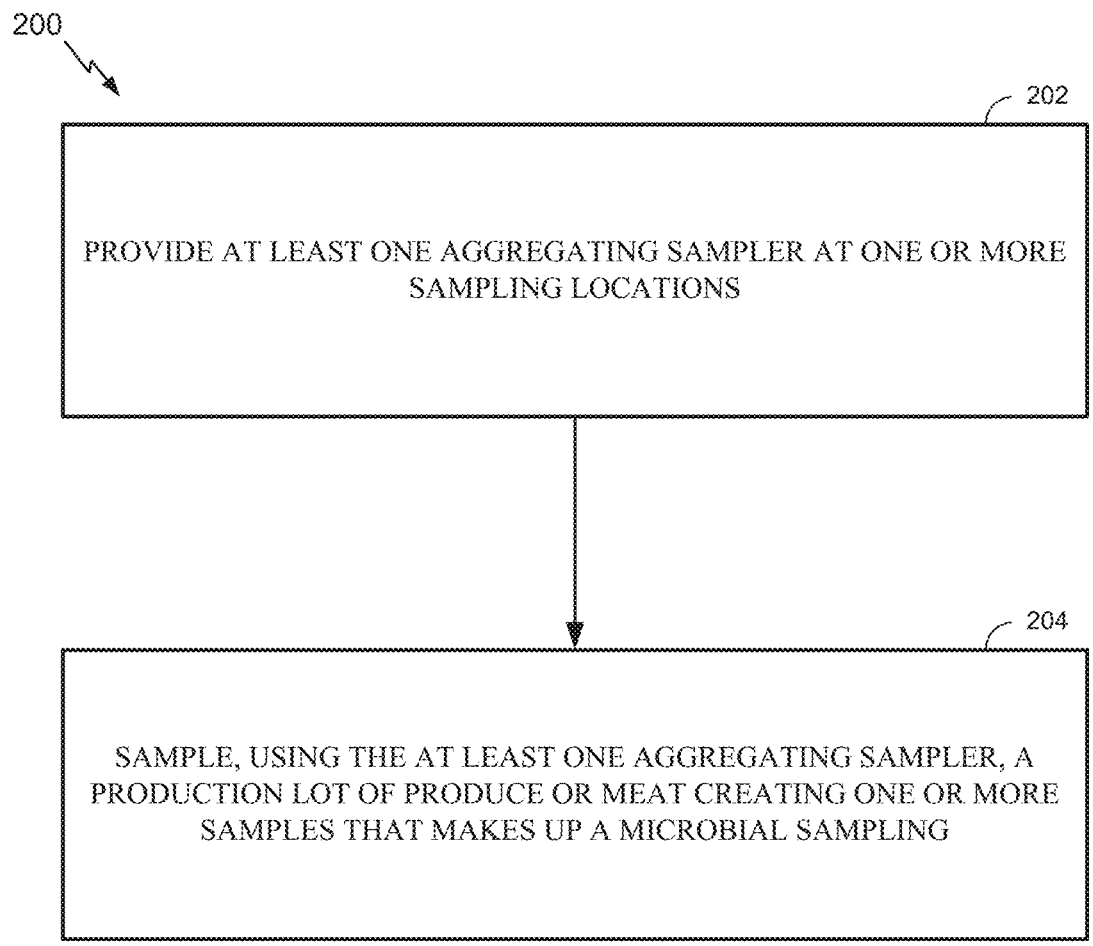
FIG. 2 illustrates example operations for applying aggregating sampling, in accordance with aspects of the present disclosure.

FIG. 2 illustrates example operations 200 for applying aggregating sampling, in accordance with aspects of the present disclosure. Specifically, operations 200 begin, at block 202, with providing at least one aggregating sampler at one or more sampling locations. Additionally, operations 200 include, at block 204, sampling, using the at least one aggregating sampler, a production lot of produce creating one or more samples that makes up a microbial sampling. The one or more samples may be configured to be processed to indicate if pathogens are present at no greater than a normal background. The one or more sampling locations may include at least one of in a field, at harvest, just after dumping or cutting, in a wash system, or after the wash system. In one or more cases, additional operations may be include such as, for example, assessing, using the aggregating sampler, a level of cross contamination control to validate or verify a wash process.

In one or more cases, an aggregating sampler may be provided that sufficiently samples a production lot of ready-to-eat produce to confirm that pathogens are present at no greater than the normal background. In one or more cases, an aggregating sampler may assess the level of cross contamination control to validate or verify a wash process.

In one or more cases, an aggregating sampler and a sampling location of the aggregating sampler may be provided. Additionally, sampling by the aggregating sampler may be provided to generate one or more desired samples. Analysis of the one or more samples and interpretation of the analysis results may also be provided. These elements can be practiced individually or together to enhance food safety.

The aggregating sampler may include a collection surface and an apparatus for holding and positioning the collection surface such that the collection surface contacts product that is to be sampled for micro-organisms or other targets. In one or more cases, a surface with a sampling efficiency that allows an increased effective sampling size when a production lot of the product is sampled may be provided. For example, two hours of production of a leafy green product may be sampled with such a device. During the two hours a large amount, for example 10,000 to 30,000 pounds, of product will have crossed the sampling surface. If the sampling device is at least 25% efficient as shown in bench scale studies, the effective sample size may be 2500 to 7500 pounds. These sample sizes are enormous when compared to the few hundred grams of a normal grab sample.

In one or more cases, there are a number of factors to consider in selecting or designing an aggregating sampler. Initially, a sampling surface that is compatible with the product is provided. This typically means that the sampling surface is a food grade material. For example, in one or more cases, a non-woven polyolefin cloth has proven to be effective. Another factor may include a design that allows safe and rapid exchange of the sampling surface. Another factor that may be included relates to any apparatus left on the line being easily cleaned and may incorporate a sanitary design. For example, food grade stainless steel may be a material selected when implementing an aggregating sampler.

For produce testing, there are a number of areas where aggregating sampling may yield improvements in food safety. For example, some locations include: 1) In the field; 2) At harvest; 3) Just after dumping or cutting; 4) In the wash system; or 5) After the wash system. In each area, there are particular locations that may be selected for aggregate sampling, but these will vary with the configuration of the specific line and the product to be sampled. Not all areas will be appropriate for all products. The selections may be guided by the desired information. Currently, grab samples are often taken in all of these areas but these grab samples are unable to represent the population under examination and such sampling is generally destructive.

According to an example, an aggregating sampler may be provide that can replace the current practice of taking a grab sample in a field by cutting leaves. Particularly, the aggregating sampler can be configured such that it can be carried by hand or mounted on a device designed for traveling through the field. The collection surface for field sampling may be divided to allow more conformity to the crop surface.

According to another example, at harvest, an aggregating sampler may be placed on the harvester such that product is sampled during the harvesting process. This approach would allow pairing of harvested product with specific information. Although not required, placement of the aggregating sampler may be just after any sorting is done in the field. For example, if rocks are sorted from the product by density classification, these rocks need not cross the sampler surface.

In another example, just after dumping or cutting and before washing, the product may still have the flora found in the field. An aggregating sampler placed early in the process can sample these organisms. Just after cutting or chopping, the interior of some products will be exposed for the first time allowing a more representative sample to be taken.

In a wash system, an aggregating sampler can collect a different type of sample in accordance with one or more examples. This sampler may test the cross contamination control of the wash system. The organisms collected will reflect the two most probable mechanisms of cross contamination, water mediated cross contamination and product to product cross contamination. An aggregating sampler, placed in the flow of the conveyed product will be impinged by both the water and the product. To avoid overly hindering product flow depending on the line design, the sampler can be placed at any angle from parallel to the product flow to complete perpendicular to product flow. The sampler can also be a comb-like device with multiple collecting probes among product and in the wash flow. The angle of attachment may affect the balance between water mediated cross contamination and product to product cross contamination observed. In either case, this type of sampling may be used to validate cross contamination control and effectiveness of wash solution.

Sampling in the wash system is a case where the sampling surface may be active on multiple surfaces, for example, on both sides or around in the case of the comb like structure mentioned above. In one or more cases, it can prove advantageous to laminate two sheets together with an impermeable tie layer to increase the binding potential relative to the detachment potential by avoiding flow through the sampling surface. Additionally, further advantages may be provided in other ways such as by increasing the thickness of the sampling material. In some cases, designing samplers in devices such as filter housing may be provided. In other cases, placement on a sampling surface in an active area of the wash system may be provided for getting a full measure of the cross contamination potential.

A sample may be taken after the wash system and will reflect a residual population. In this area there are a number of specific locations that can be considered depending on the specifics of the line. For example, these specific locations include just prior to loading dryers, in a conveyer that might be used to lift the product for packaging, just before a pocket scale, or in the throat of a form fill and seal machine. This in-line continuous sampling may significantly increase sampling efficiency and provide more meaningful data than grab sampling of finished product testing.

With samples taken, attention may turn to the analysis and interpretation of results as discussed herein. For example, in the specific category of produce, there are specific opportunities to be considered that may be provided with the aggregated sampling using the aggregated sampler. The opportunities are afforded in part due to the more representative nature of the aggregated samples and the greatly increase numbers of organisms available in the samples relative to the typical grab sample. These samples may be analyzed to give multiple channels of data depending on the detector technology employed. In one or more cases, the sample may be analyzed with metagenomics, allowing for the whole population to be studied yielding a large and in some cases a maximum amount of data which can be mined in various ways to gain knowledge and understanding of positive and negative deviations. This range of possibilities can be illustrated with a number of examples but are not limited thereto.

In one or more examples, the samples taken in the field, at harvest, or just prior to washing can be used to assess the microbiological status of the raw material. From a food safety perspective the focus heretofore has been on the presence or absence of pathogens. Unfortunately, such analyzes based on grab samples are unable to truly answer the question as to whether pathogens are present due to their lack of sensitivity. Generally, it is known that pathogens are present at very low numbers. These are ubiquitous organisms. A more appropriate question is whether these organisms are present at abnormal concentrations or without the usual competing organism.

In one or more examples, samples taken just prior to washing may be compared to samples taken in the wash system to directly measure cross contamination using wild type flora. Water samples may tend to have very low microbial loads in properly managed wash systems even when cross contamination is occurring. The wild type flora may also be highly variable. However, by using aggregating samplers at both locations the noise can be dampened and cross contamination measured. A number of metrics for cross contamination can be considered based on the ratio of the results for the samples from prewash to those from in the wash. By using more sophisticated analytical procedures one can overcome the flaws in such metrics as aerobic plate count (APC) which would include many organisms that are not relevant to cross contamination control of pathogens. For example, spore forming bacteria such as *Bacillus* will be unaffected by the wash and just cloud any metric of cross contamination based on APC. However, with more focused channels of data as afforded by modern molecular techniques better information can be obtained. Another aspect of this tool that may be provided is that statistical process control can be applied to detect deviations.

In one or more cases, samples from after a wash process may provide information about microbial populations on the finished product. These samples may provide a much more accurate assessment of the pathogen risk of the product and better detection deviations. These samples can also be used to check for deviations in the normal flora.

In some cases, a ratio between the before wash samples and the after wash samples may be used to assess the impact of the wash process. The aggregating samplers may reduce the noise and as with the cross contamination metrics, these ratios can be handled with statistical process control to look for deviations.

One or more of these examples may be delivered in almost real time because the aggregating samplers collected enough cells for concentration and direct analysis without enrichment.

Examples of Sampling: Bench Scale Examination of Sampling Efficiency for Raw Beef In accordance with one or more cases, an example of a bench scale study demonstrates a sampling efficiency of 15-20% relative to stomaching. It also shows that transfer is essentially instantaneous and that repeated contact collects more organisms. These observations confirm the intuitive assertion that continuous sampling will yield better information than grab sampling.

For example, for one bench scale study experiment, purchased stew meat is inoculated by immersion in a mixed culture of generic *E. coli* at ~105 CFU/ml. *E. coli* is selected as benign and easy to enumerate. The stew meat is allowed to rest at room temperature for 30 minutes to allow adherence. Then the six treatments listed in the table shown in FIG. 3 may be executed in 5 replicates. All sampling cloths may be cut in half, 12 in by 8 in, to reduce the sample requirement and facilitated execution of the experiment. The sampling cloth may be, for example, a MicroTally cloth but is not limited thereto. The surface areas of the meat cubes are measured directly. For the sampling cloth treatments, meat is arranged in a 10 cm by 10 cm block and the sampling cloth is applied to the upper surface. Each mini sampling cloth is extracted in 200 ml of phosphate buffered saline (PBS). As a control, cubes of stew meat are stomached for 60 seconds in 200 mL of PBS. All stomached cubes are measured to estimate surface area. The counts are normalized for surface area and averaged. This normalization provides an apple to apple comparison.

This bench scale study experiment has been implemented and the average results are tabulated and shown in Table 1 of FIG. 3. These were analyzed with a General Linear Model (GLM) model which indicates that time of contact was not a factor. Multiple contacts yielded about the expected increase and are truly additive.

A logical extrapolation of this exercise is to estimate the effective sample size of a sampling. This may not truly be possible given the differences in geometry. However, in one or more use cases when using one side only, a sampling cloth is about 6 times larger than those used in the bench scale study experiment and the intended use is to sample almost 2000 pounds of product. Thus, it is reasonable to assert that the effective sample is expected to be 300 to 400 pounds. Larger scale experiments may be implemented that may further confirm this estimate. In summary, a benefit and advantage of the above method and apparatus of sampling may include providing an improvement over traditional grab samples for meat sampling by providing larger effective samples.

Examples of Sampling: Bench Scale Examination of Sampling Efficiency for Lettuce In accordance with one or more cases, an example of a bench scale study demonstrates a sampling efficiency of about 30% relative to stomaching. It also shows that transfer is essentially instantaneous and that repeated contact collects more organisms. These observations confirm the intuitive assertion that continuous sampling will yield better information than grab sampling for lettuce.

For example, in accordance with a bench scale study experiment, purchased lettuce is inoculated by immersion in a mixed culture of generic *E. coli* at ~105 CFU/ml. *E. coli* is selected as benign and easy to enumerate. The lettuce is allowed to rest at 4° C. for 30 minutes to allow adherence. This short time may explain the higher efficiency observed when compared to a meat study where adhesion maybe faster. Then the six treatments listed in Table 2 shown in FIG. 4 may be executed in 5 replicates. All sampling cloths may be cut in half, 12 in by 8 in, to reduce the sample requirement and facilitated execution of the experiment. The sampling cloth may be, for example, a MicroTally cloth but is not limited thereto. The surface areas of the lettuce leaves may be measured directly. For the sampling cloth treatments, lettuce is arranged in a 10 cm by 10 cm block and the sampling cloth applied to the upper surface. Each mini sampling cloth is extracted in 200 ml of PBS. As a control, lettuce may be stomached for 60 seconds in 200 mL of PBS. All stomached leaves are measured to estimate surface area. The counts are normalized for surface area and averaged. This normalization provides an apple to apple comparison.

This bench scale study experiment has been implemented and the average results are tabulated and shown in Table 2 of FIG. 4. These were analyzed with a GLM model which indicates that time of contact was not a factor. Multiple contacts yielded about the expected increase and are truly additive.

A logical extrapolation of this exercise is to estimate the effective sample size of a sampling. This may not truly be possible given the differences in geometry. However, in one or more use cases when using one side only, a sampling cloth is about 6 times larger than those used in the bench scale study experiment and the intended use is to sample almost 2000 pounds of product. Thus, it is reasonable to assert that the effective sample is expected to be 400 to 600 pounds. Larger scale experiments may be implemented that may further confirm this estimate. In summary, a benefit and advantage of the above method and apparatus of sampling may include providing an improvement over traditional grab samples for leafy sampling by providing larger effective samples.

In one or more cases, swabs and/or sheets, referred to generally as a sheet below, may be used in accordance with one or more embodiments of the present disclosure. A sheet may include a microbial sampling material, such as sterile woven and/or non-woven synthetic fabrics and non-woven cloth for sampling and testing in the field of food safety. These sheets can be folded and curved to allow better conformation to product (e.g., food) streams that are being sampled or when used in a manual mode as driven by the product and the container. In some cases, configurations for sampling raw products or materials may include a sampling device that moves across the stationary product effectively yielding the equivalent of a product stream when sampling needs to occur prior to harvest. In some cases, configurations may include tail shaped sheets similar to, for example, the tentacles of a jellyfish.

In one or more cases, configurations may be provided that may provide easier use under some conditions. In one case, a microbial aggregating sampler, may include a covering including a microbial sampling material with a pocket formed in the covering to receive an appendage or a tool for handling of the covering.

In some cases, the covering may further include an attachment feature formed in the pocket to receive the tool. The attachment feature may include at least one of a hole formed through the covering; a loop positioned within the pocket to receive an end of the tool there through; or a tab positioned within the pocket for an end of the tool to attach thereto.

In some cases, the covering may include a sheath formed in the pocket to receive a digit of an appendage. In some cases, the pocket is formed through the covering such that the appendage or the tool for handling the covering extends through the covering. The covering may be completely formed from the microbial sampling material. In some cases, the covering includes two sheets attached to each other to form the pocket. In some cases, the covering may include a single sheet folded and attached to itself to form the pocket.

For example, a sheet may undergo folding and seaming to form a bag or pocket that can be worn as a mitten, glove, sock, or other covering, to facilitate manual sampling. Such a covering may encase an appendage, such as a hand, to facilitate pushing and pulling of the sampler through the product to be sampled. In some cases, aggregating samplers may be created that are more hand like configurations as mitts with thumbs and/or gloves with fingers, allowing the sampler to better conform to the hand. Such configurations may allow easier use when the product is more viscous or more prone to adhering to the sampler. A benefit to this aggregating sampler with a pocket may include the ability of the sampler to, when working the sampler, increase or maximize product contact. Further, in some cases, the addition of one or more attachment features, such loops or tabs, to assist with controlling the product contact may be included. These are representative examples and are not meant to limit other configuration embodiments of an aggregating sampler.

In some cases, the aggregating sampler may be used in an automated machine setting to sample a product stream. The aggregating sampler may include a number of modifications in accordance with one or more cases. In some cases, the aggregating sampler may include one or more bends and curves that may improve the utility and facilitate use. In some cases, modifications may include, but are not limited to, forming a tube that can slide over one or more shafts for positioning in the product flow. This configuration may remove the need to slide the sampler within any holding device. In some cases, adding tabs or holes can be provided which may allow positioning and facilitate attachment. In some cases, the active sampling surface can be attached to a support material or web that has one or more of these features. One or more of these cases and modifications may help facility contact with the product stream with minimal manual intervention.

Figure 5:
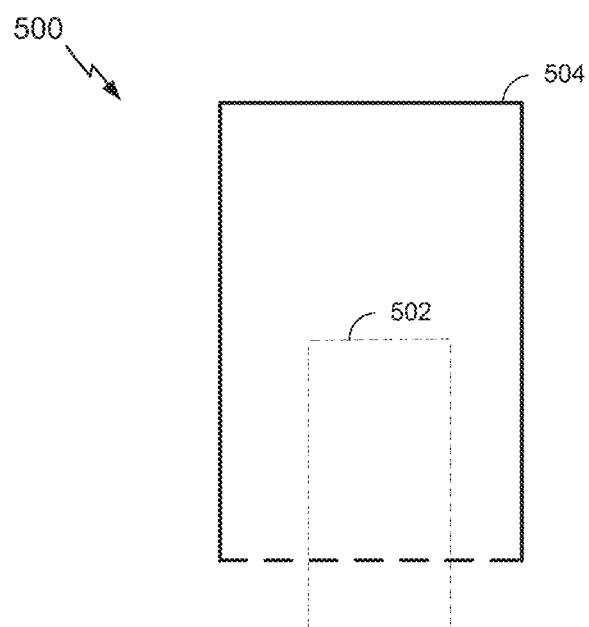
FIG. 5 illustrates an aggregated sampler that includes a pocket in accordance with aspects of the present disclosure.

FIG. 5 illustrates an aggregated sampler 500 that includes a pocket in accordance with aspects of the present disclosure. As shown the aggregated sampler 500 includes a covering 504 made of a microbial sampling material. The covering is formed such that it includes a pocket formed in the covering to receive an appendage or tool 502 within the pocket for handling of the covering.

Figure 6:
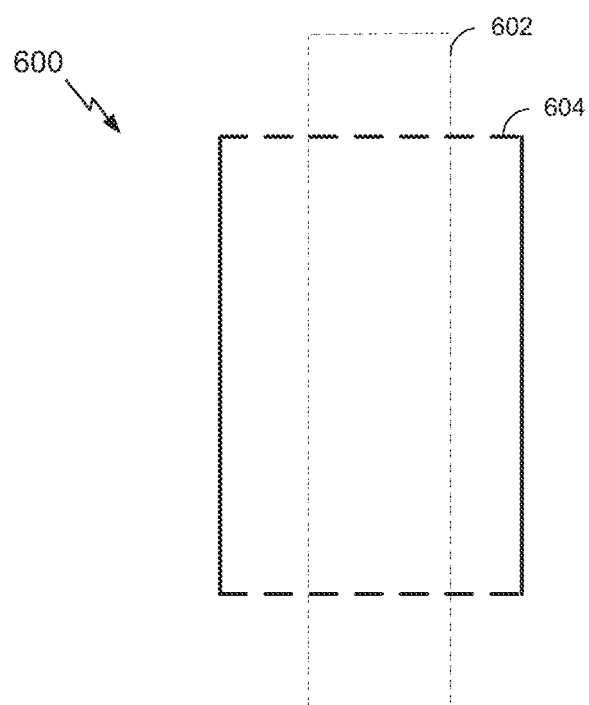
FIG. 6 illustrates an aggregated sampler that includes a pocket that extends through a covering in accordance with aspects of the present disclosure.

FIG. 6 illustrates an aggregated sampler 600 that includes a pocket that extends or is formed through a covering 604 in accordance with aspects of the present disclosure. The pocket is formed such that the appendage or tool 602 for handling the covering 604 extends through the covering.

Figure 7:
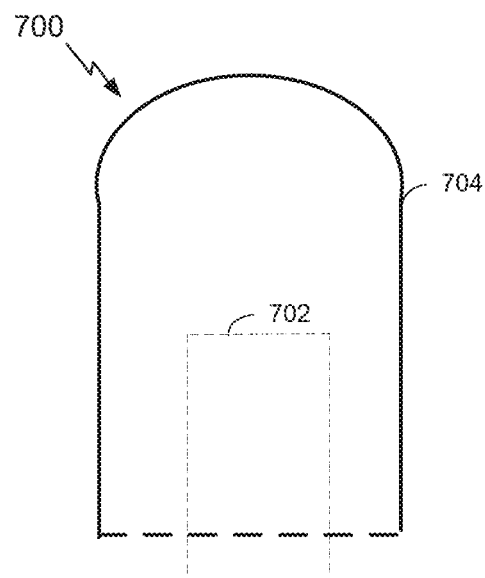
FIG. 7 illustrates an aggregated sampler with at least one convex surface in accordance with aspects of the present disclosure.
Figure 8:
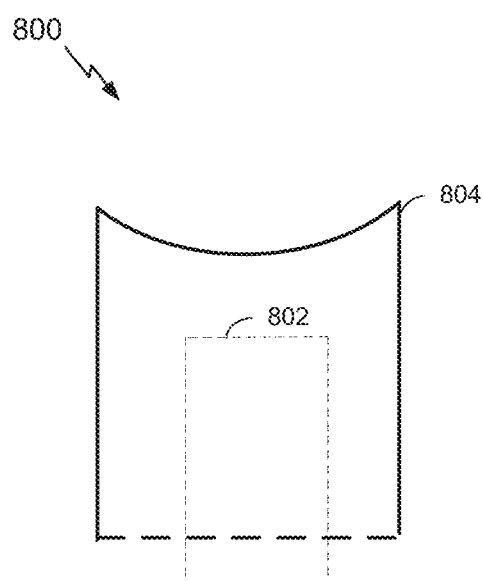
FIG. 8 illustrates an aggregated sampler that includes at least one concave surface in accordance with aspects of the present disclosure.
Figure 9:
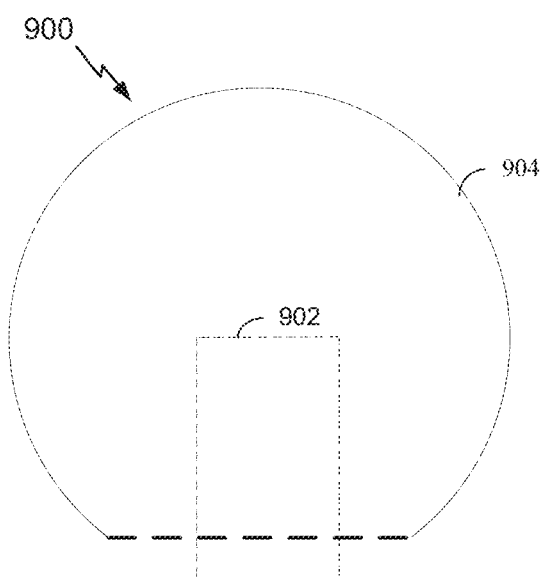
FIG. 9 illustrates an aggregated sampler that includes a curved shape in accordance with aspects of the present disclosure.

FIG. 7 illustrates an aggregated sampler 700 with at least one convex surface of the covering 704 in accordance with aspects of the present disclosure. The covering forms a pocket for a tool or appendage 702. FIG. 8 illustrates an aggregated sampler 800 that includes at least one concave surface of the covering 804 in accordance with aspects of the present disclosure. The covering 804 forms a pocket for a tool or appendage 802. FIG. 9 illustrates an aggregated sampler 900 that includes a curved shape covering 904 in accordance with aspects of the present disclosure. The covering 904 is formed to include a pocket for a tool or appendage 902.

Figure 10:
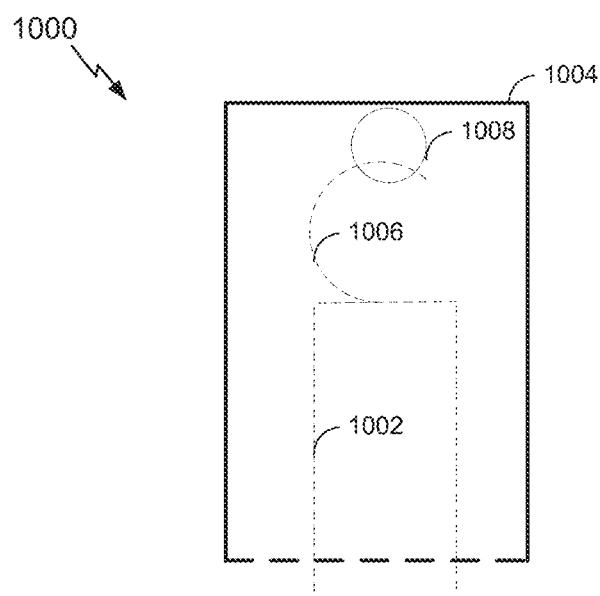
FIG. 10 illustrates an aggregated sampler that includes a hole or loop in accordance with aspects of the present disclosure.

FIG. 10 illustrates an aggregated sampler 1000 that includes a hole or loop 1008 in accordance with aspects of the present disclosure. The covering 1004 may include the hole or loop 1008, such as positioned within the pocket of the covering 1004 and attached to an inner surface of the covering 1004. This hole or loop 1008 may be used by a hook 1006 of a tool 1002 to attach to the covering 1004.

Figure 11:
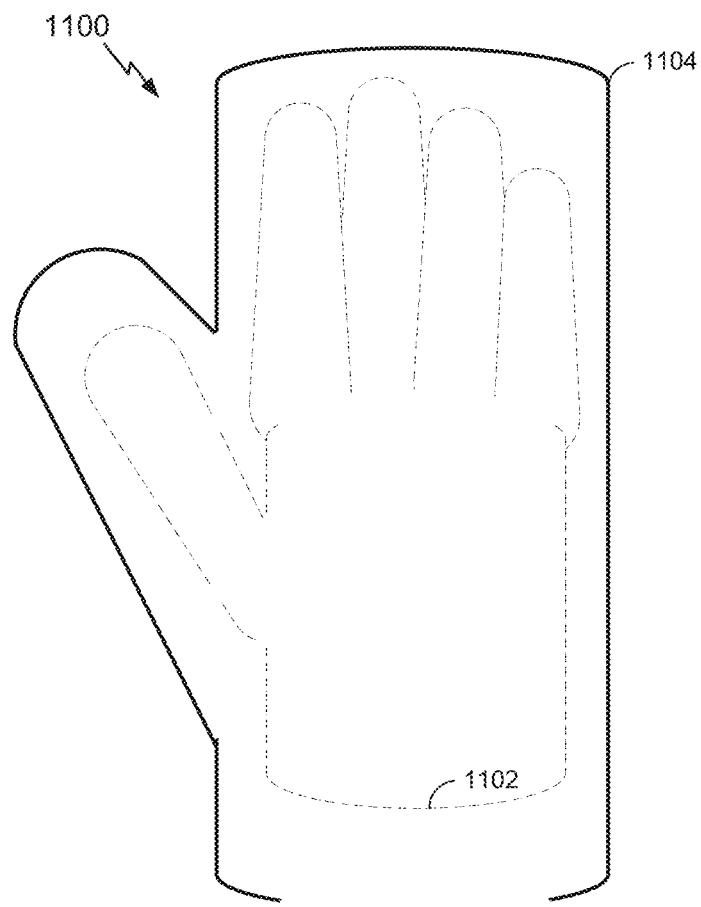
FIG. 11 illustrates an aggregated sampler that is shaped as a mitten or glove for a hand in accordance with aspects of the present disclosure.

FIG. 11 illustrates an aggregated sampler 1100 that is shaped as a mitten or glove for a hand 1102 in accordance with aspects of the present disclosure. As shown, the covering 1104 of the aggregated sampler 1100 is formed to contour to a hand 1102. In particular, a sheath is formed in the covering 1104 in this embodiment to receive a thumb of the hand 1102, though one or more sheaths may be used to receive any digit of the hand 1102. Further, though only a hand 1102 is shown as an example appendage in this embodiment, the present disclosure is not so limited, as other appendages (i.e., a foot) may be contemplated for other embodiments without departing from the scope of the present disclosure.

In accordance with one or more cases, the aggregated sampling sheet may be hung into an active zone of a wash line with a cord or cable. This line may be attached in number of ways to the sampling material such as, for example, a grommet and clasp. In some cases, a ball and slide clamp may be used. In some cases, a punched hole may be used but may pull out. In other cases, various other clamps may be used. In one or more case, an optional float such as a fishing float with or without a weight may be included that will add drag and bouncy which may improve surface exposure. This approach may not include a fixed appliance for holding the sampling material.

Examples of Mobile Aggregating Sampler

In one or more cases, a microbial aggregating sampler may be mobile to facilitate use in various environments and industries. Food safety is an important factor, if not the most important factor, in the food industry. This level of safety also applies in many other industries that include consumable products, such as within agriculture, pet food, and dietary supplements. The goal with safety is to eliminate all or as many pathogens as possible from the consumable products. Aggregating samplers enable measurement and study of pathogens and other micro flora, even at low levels.

However, the diversity of consumable product flow lines, locations, and environments for such sampling requires flexibility for the aggregating sampler, and thus increases the need for mobility of an aggregating sampler.

Accordingly, in accordance with one or more cases of the present disclosure, an aggregating sampler may include a mobile frame, such as a wheeled frame, that is presents one or more sampling sheets or a roll of microbial sampling material at an end of a conveyor or chute that provides a cascade of consumable products for sampling. The aggregating sampler may additionally or alternatively use one or more cassettes that include the sampling sheets, such as through a stacked cassette feeding system, to collect samples in the aggregating sampler without any or minimum manual intervention.

The aggregating sampler may be mobile by attaching one or more wheels (e.g., three or four wheels) with or without locking brakes. The wheels may be individually lockable and unlockable (e.g., actuated), or may be actuated collectively using a single lever or actuator, such as actuated when being pushed. In another aspect, one or two wheels may be coupled to the frame of the aggregating sampler to provide mobility, such as to allow tilting or pushing of the aggregating sampler similar to a hand truck. The wheels may be coupled to the frame and/or a lower plate or platform to provide stability for the aggregating sampler. The wheels may be movable (e.g., raised or lowered) within the aggregating sampler, such as through the wheels being mounted on levers to the mobile frame, or by having the wheels hooked into channels or apertures formed within the frame. Alternatively, the wheels may be replaceable by skits or pads to enable the frame of the aggregating sampler to be mobile.

In one or more embodiments, the aggregating sampler may include legs or feet that are adjustable with respect to each other or the mobile frame, such as to level the aggregating sampler on an uneven floor or even lift the wheels off the floor. The spacing of the wheels can be increased to afford stability to the aggregating sampler, particularly given that energy is received by the aggregating sampler when consumable products flow, contact, and impact the aggregating sampler.

The aggregating sampler may be manually movable, such as by pushing or pulling the mobile frame of the aggregating sampler, or may include one or more motors for automated movement. For manual movement, one or more handles may be coupled (e.g., movably coupled through an arm) to the mobile frame of the aggregating sampler and may removable from the mobile frame for ease of cleaning and sanitation. A hitch may be included with the aggregating sampler to hitch or couple the aggregating sampler to other aggregating samplers and/or other devices for movement or for use. For example, the aggregating sampler may be hitched or coupled to a cart, vehicle, or robot for deployment within a facilitate, and/or may be hitched or coupled to a conveyor or other food processing unit during use that provides the consumable products to the aggregating sampler for sampling.

In some embodiments, the aggregating sampler is designed, such as through material selection and in configuration, to facilitate cleaning and sanitation, as the aggregating sampler should not be a source of contamination. The aggregating sampler will generally not include porous materials, such as wood or sponges, for softer surfaces or corners. Materials that are food contact approved and regulated, as discussed more below, may be used. Further, the aggregating sampler, and particularly the mobile frame, may avoid having internal spaces that may harbor contamination. Thus, open channels rather than round or square tubes for the frame may be used, and joints of the mobile frame may be able to disassemble into smaller sub-components or parts to facilitate cleaning. Structural members (e.g., supports as described below) of the mobile frame may comprise angle iron or be U-shaped to avoid enclosed spaces. The mobile frame may be formed from one to four different structural members forming the entirety of the mobile frame for the aggregating sampler to facilitate cleaning. The structural members may also be interlaced with each other or overlap to enable adjustments (e.g., in height or in width) for the mobile frame. Holes may be formed through the structural members to receive fasteners, such as clevis pins, to enable the adjustment of the mobile frame. Further, fasteners used to assemble the mobile frame and couple the other components to the mobile frame within the aggregating sampler may be tethered to the mobile frame, such as through cables, to prevent loss of the fasteners within the consumable product when flowing across the aggregating sampler for sampling. Further, welds and joints for the mobile frame of the aggregating sampler should be leveled or flattened, at least partially, to facilitate cleaning.

In one or more aspects, the aggregating sampler may be used to receive product through one or more different interactions in a food processing environment. For example, the aggregating sampler may be used to catch product, such as from a worker tossing or throwing meat (e.g., beef trim) at the aggregating sampler for sampling. Alternatively, the aggregating sampler may be used to collect product that is conveyed or slid into the aggregating sampler from a food processing device. As such, the aggregating sampler may include a cowling to facilitate receiving consumable product within the aggregating sampler for sampling the consumable product.

The angle of the surface of the aggregating sampler (e.g., a guide surface and/or a sample surface positioned within the aggregating sampler) may be used to enable a downward and motive force of the consumable product along through the aggregating sampler. A greater angle of the guide surface and/or the sample surface with respect to a horizontal plane increases the motive force of the consumable product through the aggregating sampler. A lower angle the guide surface and/or the sample surface with respect to a horizontal plane increases the ability of the sample surface to effectively sample the consumable product through the aggregating sampler.

In one or more aspects, and as discussed more below, a sampling sheet (which includes a microbial sampling material) may be removably secured to a surface (e.g., a sample surface) of the aggregating sampler using one or more fasteners. The fasteners may include clips or a clamping type device to facilitate removably securing the sampling sheet within the aggregating sampler. In another aspect, as also discussed more below, a cartridge or cassette mechanism may be used, in which the sampling sheet is removably secured within the cartridge. The cartridge may then be removably secured within the mobile frame of the aggregating sampler, such as by sliding the cartridge into slots.

In one or more aspects, a cartridge holder and/or conveyor may also be employed that moves multiple cartridges, or only the sampling sheets without a cartridge, into and out of a flow path of the consumable product. For example, a sampling conveyor may be included that moves with respect to the mobile frame to move sampling sheets with respect to the mobile frame. The sampling conveyor may be rotatable with respect to the mobile frame, such as similar to a turret, and/or may be translatable (e.g., moves side-to-side or up-and-down) with respect to the mobile frame. The sampling conveyor may move parallel to the flow of the consumable product through the aggregating sampler, and/or may move perpendicular to the flow of the consumable product through the aggregating sampler. The sampling sheets are then removably secured to the sampling conveyor, such as separately through fasteners or with each sampling sheet positioned upon a cartridge with the cartridge removably positioned within the sampling conveyor.

The actuation of the movement of the sampling conveyor may be timed based upon one or more factors of the food processing operation. For example, if the consumable product is loaded into bins, the sampling conveyor may move to introduce a new sampling sheet into the consumable product stream as each bin is filled and is changed. The actuation of the sampling conveyor may be timed based, or could be based upon a predetermined volume or mass for the consumable product. A covering or a shielding may also be used for sampling sheets not positioned within the product stream (e.g., not in use) to prevent contamination on those sampling sheets, even when other sampling sheets are in use within the sampling conveyor.

Further, in one or more aspects, the sampling sheet may include a roll or a web of microbial sampling material. The roll may be used to rotate with respect to the mobile frame of the aggregating sampler to distribute the microbial sampling material perpendicular (or parallel) to a flow path of the consumable products through the aggregating sampler. For example, the roll may be positioned under the product flow, such as underneath the guide or sample surface, so that feeding of the roll does not interfere with the operation and product flow of the aggregating sampler. The roll may also feed across the product flow. The roll may also be positioned within a roll housing to facilitate dispensing the microbial sampling material therefrom. The roll housing may be similar to that of a film canister, in which a slit may be formed in the roll housing to distribute the roll therefrom and may apply a predetermined amount of tension across the roll.

To facilitate a roll feeding embodiment, impermeable sections may be included within the roll between sections of microbial sampling material and/or an impermeable backing may be included within the roll to isolate samples (e.g., sampling sheets) from each other. In one or more embodiments, a sampling sheet dispenser may be used to dispense the sampling sheets. In such an embodiment, a feed or a roll of sampling sheets may be dispensed into the flow of the consumable product. For example, perforations may be included within sampling sheets for the dispenser to engage the perforations when dispensing the sampling sheets. The perforations may later be removed, such as by having line-tearing features formed within the sampling sheets.

Figures 12, 13:
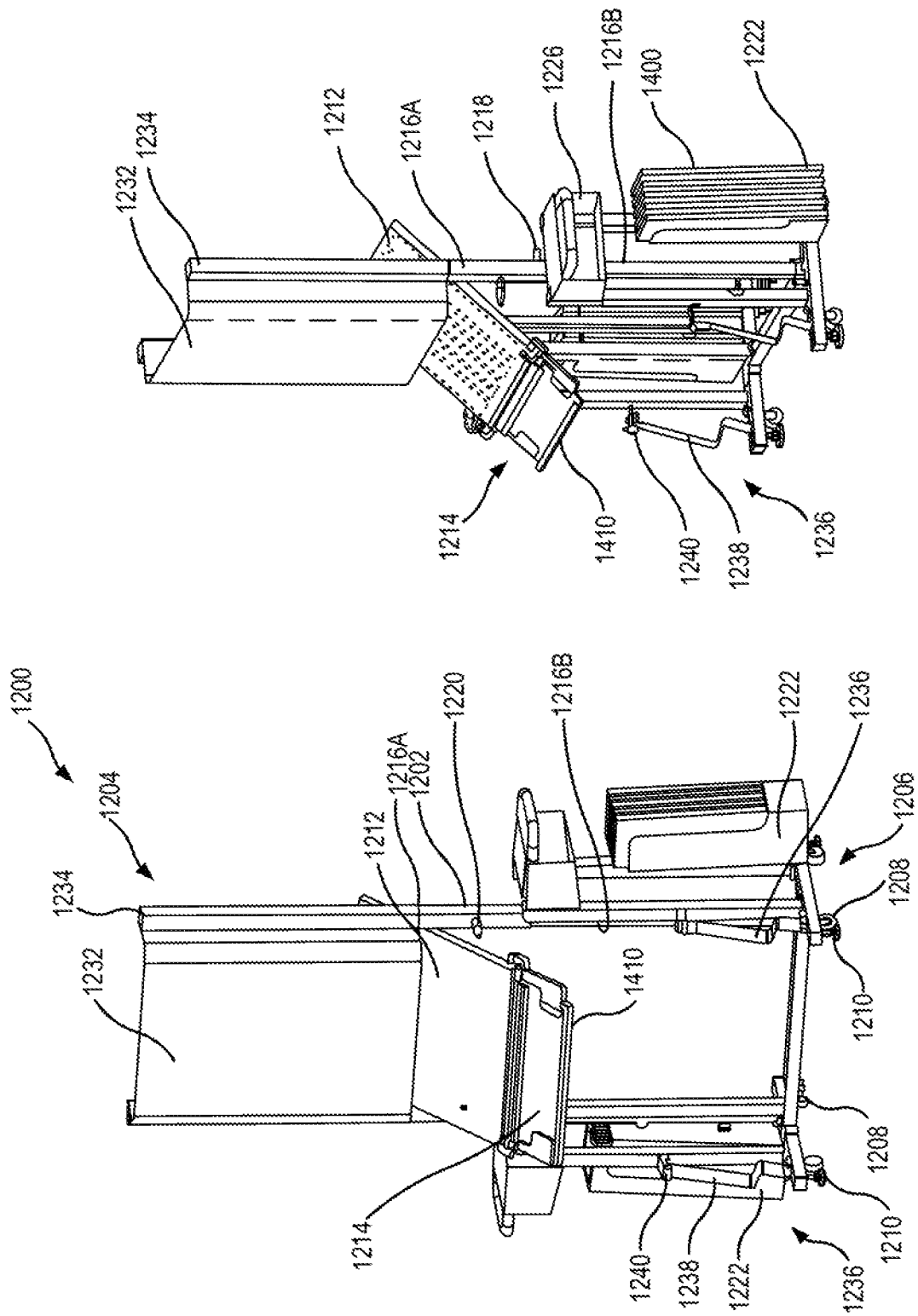
FIG. 12 illustrates a mobile aggregating sampler that includes a mobile frame in accordance with aspects of the present disclosure.
FIG. 13 illustrates the aggregating sampler in accordance with aspects of the present disclosure.

Accordingly, FIGS. 12 and 13 illustrate an aggregating sampler 1200 that is mobile in accordance with aspects of the present disclosure. The aggregating sampler 1200 includes a mobile frame 1202 with an upper end 1204 and a lower end 1206, such as when in an upright position shown in FIGS. 12 and 13. The frame 1202 may be mobile by including one or more wheels or one or more pads coupled to the frame 1202. For example, multiple wheels 1208 are coupled to the lower end 1206 of the frame 1202 to enable movement and mobility for the frame 1202. The wheels 1208, or one or more of the wheels 1208, may be lockable to prevent rotation of the wheels 1208 and mobility of the frame 1202. One or more feet 1210 may also be adjustably coupled to the lower end 1206 of the frame 1202 to enable leveling of the mobile frame 1208, such as when the aggregating sampler 1200 is in position for sampling.

The aggregating sampler 1200 further includes a guide surface 1212 and a sample surface 1214 coupled to the mobile frame 1202. The guide surface 1212 and the sample surface 1214 are positioned within the mobile frame 1202 such that consumable products to be sampled (e.g., tested) using the aggregating sampler 1200 pass along each surface 1212 and 1214. The guide surface 1212 receives the consumable products within the aggregating sampler 1200 and passes the consumable products along the guide surface 1212 to the sample surface 1214. The sample surface 1214, which is positioned adjacent and may be coupled to the guide surface 1212, receives the consumable products from the guide surface 1212 and passes the consumable products along the sample 1212 and out of the aggregating sampler 1200. A sampling sheet (shown and discussed more below) that includes a microbial sampling material is removably secured on the sample surface 1214. The consumable products contact the sampling sheet when passing along the sample surface 1214, thereby enabling sampling of the consumable products with the sampling sheet. The sampling sheet may then be removed from the sample surface 1214 and the mobile frame 1202 for analysis of the sampling sheet and the consumable products in contact with the sampling sheet.

FIGS. 14 and 15 illustrate a sample surface 1214 in accordance with aspects of the present disclosure. In this embodiment, the sample surface 1214 includes a cartridge 1400. The cartridge 1400 includes a body 1402 and a cover 1404 movable (e.g., removable or rotatable) with respect to the body 1402. A sampling sheet 1406 is positioned over the body 1402 and between the cover 1404 and the body 1402. One or more fasteners 1408 (e.g., clips) are then used to removably secure the cover 1404 to the body 1402. The sampling sheet 1406 is therefore exposed through the cover 1404 and supported by the body 1402 for contacting consumable products. After use, the sampling sheet may be removed from between the body 1402 and the cover 1404 and replaced such that the cartridge 1400 may be reused.

Figure 16:
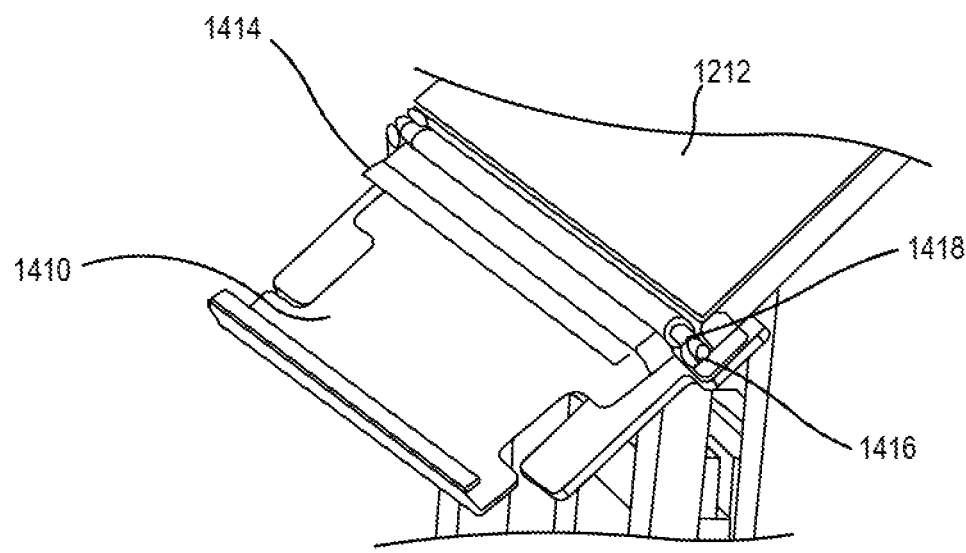
FIG. 16 illustrates a baseplate for the cartridge in accordance with aspects of the present disclosure.

The sample surface 1214 may removably coupled to the mobile frame 1202, such as through the use of the cartridge 1400. The cartridge 1400 may slidingly be removably coupled to the mobile frame 1202 through a baseplate 1410. The baseplate 1410 is coupled and secured to the mobile frame 1202, in which the cartridge 1400 may slide into a slot 1414 of the baseplate 1410 for use. A flow path 1412 shown particularly in FIG. 15 illustrates the projected path for the consumable product to pass along from the guide surface to the sample surface 1214. The cartridge 1400 may slide into engagement with the baseplate 1410 along a path perpendicular to the flow path 1412 such that the consumable product contacting the sampling sheet 1406 does not accidentally dislodge or disengage the cartridge 1400 from the baseplate 1410. Further, if desired, the baseplate 1410 may be removably coupled to the mobile frame 1202, such as through a pin 1416 and slot 1418 engagement (shown for reference in FIG. 16), to facilitate cleaning of the baseplate 1410 and the mobile frame 1202.

Referring back to FIGS. 12 and 13, the sample surface 1214 is positioned at a non-horizontal angle within the mobile frame 1202, such as when in use and when the aggregating sampler 1200 is sampling consumable products. The non-horizontal angle may facilitate the consumable products from contacting and passing along the sample surface 1214. Further, the guide surface 1212 may also be positioned at a non-horizontal angle in one or more embodiments. A non-horizontal angle may be shown in FIG. 15 as an angle A formed with respect to a horizontal plane H. In FIGS. 12 and 13, though not so limited, the sample surface 1214 and the guide surface 1212 are positioned at the same non-horizontal angle, and may even be substantially co-planar with each other. To facilitate the product flow across the sample surface 1214 and the guide surface 1212, the sample surface 1214 and/or the guide surface 1212 may be positioned at a non-horizontal angle between about 1 degree and about 89 degrees with respect to the horizontal plane H. More particularly, the sample surface 1214 and/or the guide surface 1212 may be positioned at a non-horizontal angle between about 30 degrees and about 60 degrees with respect to the horizontal plane H, and even more particularly at about 45 degrees with respect to the horizontal plane H.

The angle between the sample surface 1214 and/or the guide surface 1212 may also be adjustable with respect to each other and/or with the horizontal plane H within the aggregating sampler 1200, such as to facilitate flow for different types of consumable product through the aggregating sampler 1200. Consumable product, such as leafy greens, that is relatively less dense may require a relatively higher angle for the sample surface 1214 and the guide surface 1212, and consumable product, such as meat, that is relatively denser may require a relatively lower angle for the sample surface 1214 and the guide surface 1212.

In one or more cases, a height of the guide surface 1212 and the sample surface 1214 may be adjustable, such as by being adjustable with respect to the lower end 1206 of the mobile frame 1202. For example, the mobile frame 1202 may be formed from multiple supports 1216A and 1216B (e.g., sub-frames) that are coupled to each other. In this embodiment, the supports 1216A are shown as an upper support 1216A and a lower support 1216B that are adjustable with respect to each other. One or more fasteners, such as a lock pin 1218, may be positioned within holes formed within the supports 1216A and 1216B, as desired, to adjustably secure the supports 1216A and 1216B to each other. One or more handles 1220 may be provided on one or both of the supports 1216A and 1216B to facilitate moving and adjusting the supports 1216A and 1216B with respect to each other. Further, the lock pin 1218 may be secured to the mobile frame 1202 using a tether to prevent loss of the lock pin 1218, particularly when sampling consumable products.

One or more components of the aggregating sampler 1200, and in particular all of the components of the aggregating sampler 1200, are formed from a food grade or a food contact material. For example, the components of the aggregating sampler 1200 may be formed from a food contact material identified under 21 Code of Federal Legislation (C.F.R.) §§ 170-190, which is incorporated herein by reference for all purposes. In one embodiment, food contact material may be stainless steel or composite resin. In such an embodiment, the mobile frame may be formed from stainless steel, whereas the guide surface 1212 may be formed from composite resin. The sample surface 1214 may be formed from stainless steel and/or composite resin, such as by having the baseplate 1214 formed from stainless steel with portions of the cassette 1400 formed from composite resin.

Figure 17:
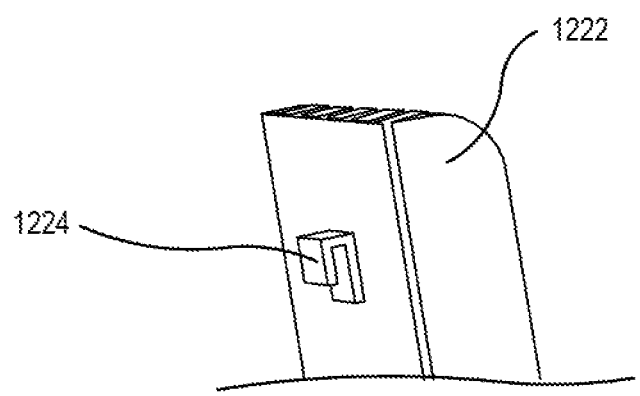
FIG. 17 illustrates a cartridge holder for a mobile aggregating system in accordance with aspects of the present disclosure.

Referring still to FIGS. 12 and 13, one or more cartridge holders 1222 may be coupled, and more so removably coupled, to the mobile frame 1202. For example, with quick reference to FIG. 17, the cartridge holder 1222 may include a hook 1224 to removably couple the cartridge holder 1222 to the mobile frame 1202. The cartridge holders 1222 may be used to removably receive one or more cartridges 1400 therein. If using more than one cartridge holder 1222, as shown in FIGS. 12 and 13, one of the cartridge holders 1222 may house unused cartridges before sampling, and another one of the cartridge holders 1222 may house used cartridges after sampling.

Figure 18:
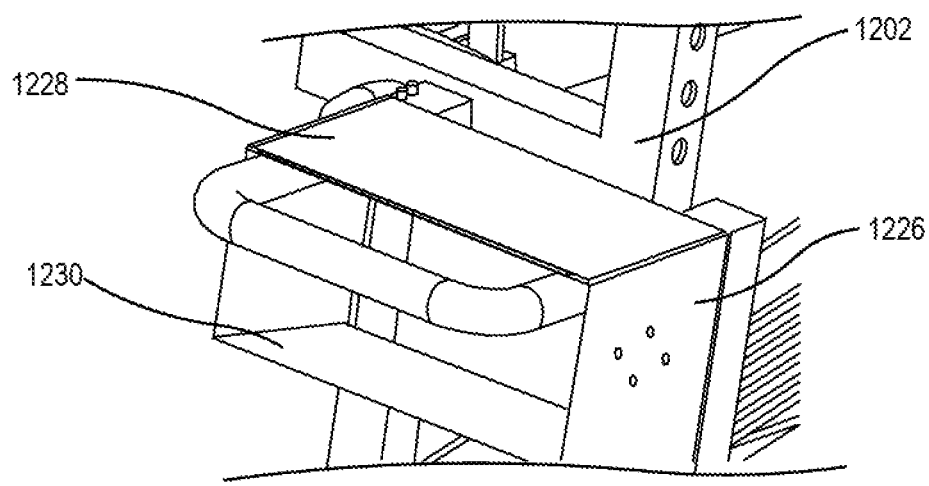
FIG. 18 illustrates a cartridge changing station for a mobile aggregating system in accordance with aspects of the present disclosure.

The aggregating sampler 1200 may further include cartridge changing station 1226. A detailed view of the cartridge changing station 1226 is shown in FIG. 18. The cartridge changing station 1226 couples to the mobile frame 1202, and may include one or more levels to facilitate changing for the cartridges 1400 and sampling sheets 1406 for the cartridges 1400. For example, the cartridge changing station 1226 includes a flat upper changing level 1228 to facilitate changing of the sampling sheets within a cassette, and includes a lower storage level 1230 to facilitate storage of used and/or unused sampling sheets.

A cowling 1232 is shown included within the aggregating sampler 1200 to facilitate having consumable products that are sampled pass along the guide surface 1212 and the sample surface 1214. The cowling 1232 is coupled, such as removably coupled, to the mobile frame 1202. In this embodiment, arms of the mobile frame 1202 are received into slots 1234 formed on opposite sides of the cowling 1232 to removably couple the cowling 1232 to the mobile frame 1202. The cowling 1232 is positioned above the guide surface 1212 and the sample surface 1214 such that consumable products that contact the cowling 1232 are routed (e.g., by gravity) to the guide surface 1212 and the sample surface 1214.

Referring still to FIGS. 12 and 13, a bin support 1236 is included within the aggregating sampler 1200 at the lower end 1206 of the mobile frame 1202. The bin support 1236 is used to support a bin that will receive the consumable products from the aggregating sampler 1200 after sampling. The bin support 1236 is shown in FIGS. 12 and 13 as one or more legs 1238 that will be received underneath a bin to couple the aggregating sampler 1200 to the bin. The legs 1238 may be movable with respect to the mobile frame 1202 between an upper position, shown in FIGS. 12 and 13, and a lower position in which the legs 1238 are folded downward and the bin is received upon at least a portion of the legs 1238. One or more release mechanisms 1240, such as a spring biased clip, may be used to retain the legs 1238 in the upper position such that the legs 1238 of the bin support 1236 are only deployed to the lower position when desired.

FIG. 19 illustrates an aggregating sampler 1900 in accordance with aspects of the present disclosure. In this embodiment, the aggregating sampler 1900 includes a guide surface 1912 and a sample surface 1914, in which both the guide surface 1912 and the sample surface 1914 may be removably coupled to a mobile frame 1902 of the aggregating sampler 1900. A plate 1940 including slots 1942 is shown coupled to the mobile frame 1902 with the guide surface 1912 received within the slots 1942 of the plate 1940. The sample surface 1912, which may include a cassette (not shown), may be positioned within slots 1946 of a baseplate 1944 with the baseplate 1944 removably coupled to the plate 1940.

FIG. 20 illustrates an aggregating sampler 2000 in accordance with aspects of the present disclosure. The aggregating sampler 2000 includes a bin support 2036 with the bin support 2036 movable (e.g., rotatable) with respect to a mobile frame 2002. In this embodiment, the bin support 2036 is shown as a plate 2038 or a step structure that is rotatable with respect to the mobile frame 2002, in which the plate 2038 is received partially underneath the bin to support the bin with the mobile frame 2002.

Figure 21:
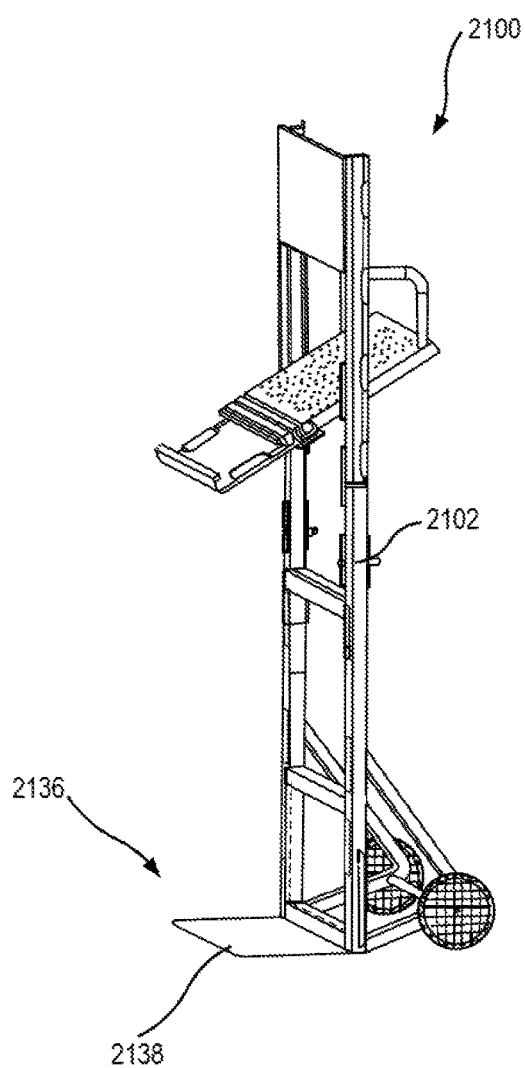
FIG. 21 illustrates a mobile aggregating sampler that includes a mobile frame in accordance with aspects of the present disclosure.

FIG. 21 illustrates an aggregating sampler 2100 in accordance with aspects of the present disclosure. In this embodiment, a mobile frame 2102 for the aggregating sampler 2100 is in a dolly or hand truck configuration. As such, a bin support 2136 is shown as a plate 2138 in which the plate 2138 is not movable but rigidly coupled to the mobile frame 2102.

Figure 22:
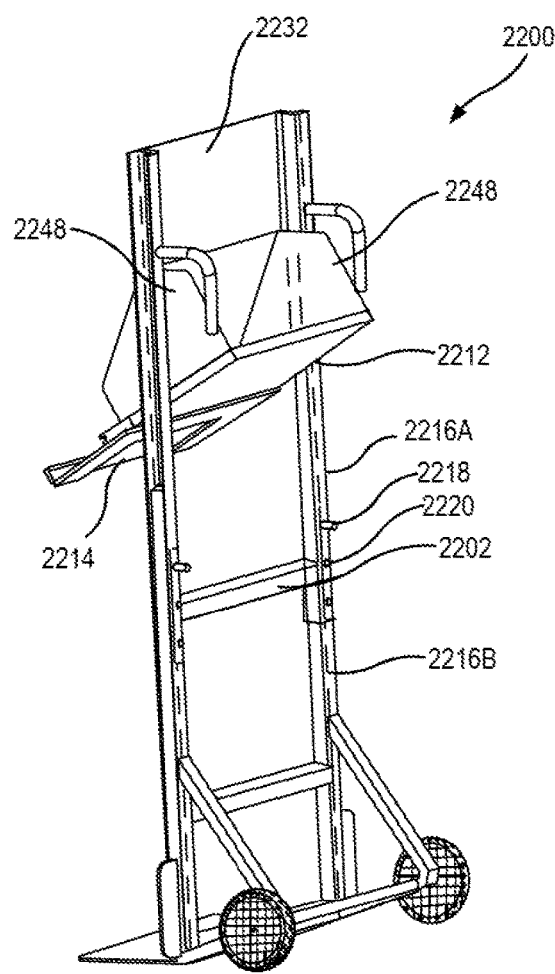
FIG. 22 illustrates a mobile aggregating sampler that includes a mobile frame in accordance with aspects of the present disclosure.

FIG. 22 illustrates an aggregating sampler 2200 in accordance with aspects of the present disclosure. In this embodiment, a mobile frame 2202 for the aggregating sampler 2200 is shown as having an upper support 2216A and a lower support 2216B that are adjustable with respect to each other. For example, lock pins 2218 may be positioned within holes 2220 formed within the supports 2216A and 2216B to adjustably secure the supports 2216A and 2216B to each other and enable height adjustment for the aggregating sampler 2200. The height adjustment for the aggregating sampler 2200 enables a guide surface 2212 and a sample surface 2214 to adjust in height with respect to a lower end 2206 of the mobile frame 2202.

In FIG. 22, one or more side guide surfaces 2248 are included with the guide surface 2212 in the aggregating sampler 2200. The side guide surfaces 2248 are coupled to or positioned adjacent to the sides of the guide surface 2212 and extend upward from the guide surface 2212. The side guide surfaces 2248 facilitate flow of the consumable product from a cowling 2232 to the guide surface 2212 along the guide surface 2212 to the sample surface 2214.

Figures 23A, 23B:
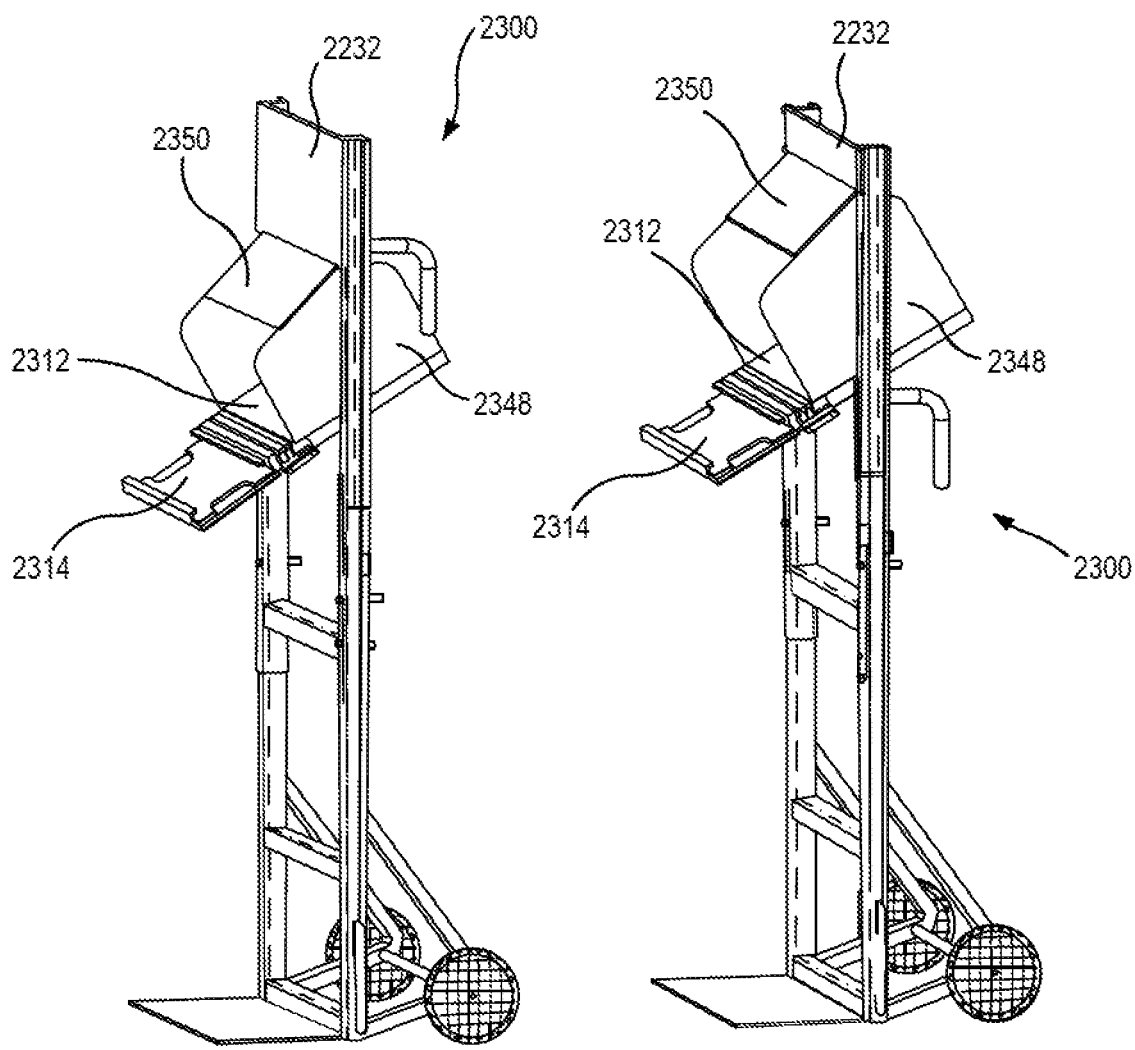
FIGS. 23A and 23B illustrate a mobile aggregating sampler that includes a mobile frame in accordance with aspects of the present disclosure.

FIG. 23A illustrates an aggregating sampler 2300 in accordance with aspects of the present disclosure. In this embodiment, side guide surfaces 2348 are included with a guide surface 2312 in the aggregating sampler 2300. Further, an above guide surface 2350 is also included with the guide surface 2312. The above guide surface 2350 is positioned adjacent or coupled to the side guide surfaces 2348 and/or a cowling 2232. The above guide surface 2350 and the side guide surfaces 2348 may define a chute to facilitate flow of the consumable product along the guide surface 2312 to a sample surface 2314. Further, the size of relative size and shapes of the guide surface 2312, the side surfaces 2348, the above guide surface 2350, and the cowling 2232 may vary, such as shown relatively in FIG. 23B, with the cowling 2232 being smaller and the side surfaces 2348 being larger in FIG. 23B, thereby defining a larger chute.

Figure 24A:
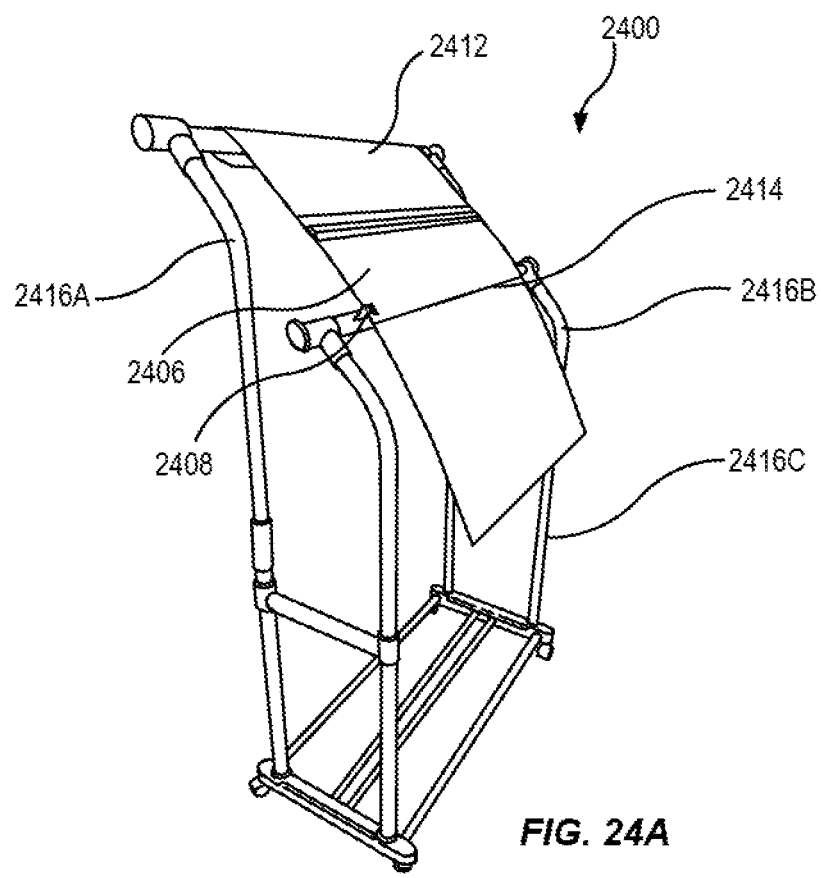
FIGS. 24A and 24B illustrate a mobile aggregating sampler that includes a mobile frame in accordance with aspects of the present disclosure.
Figure 24B:
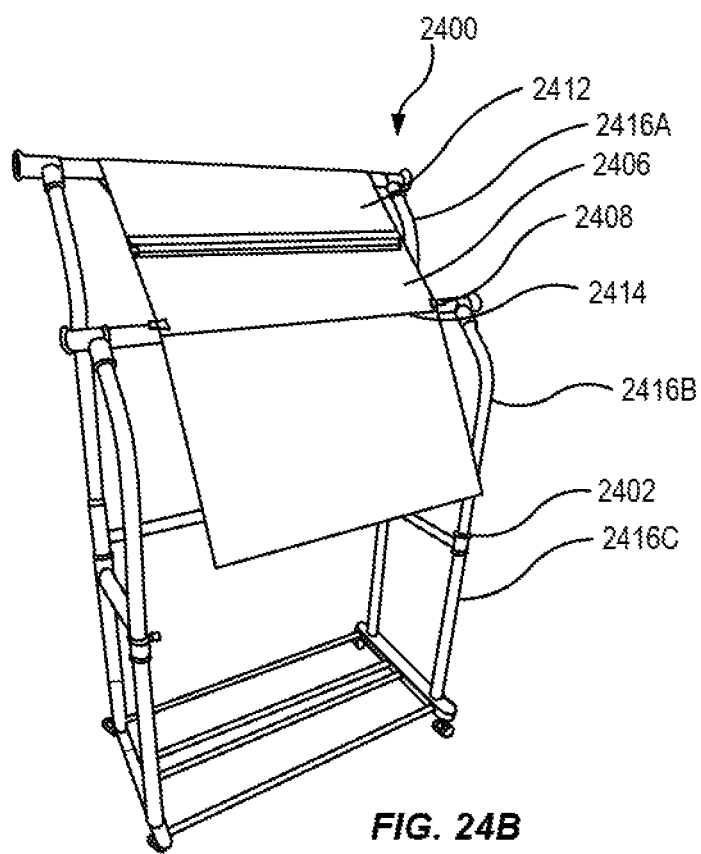

FIGS. 24A and 24B illustrate an aggregating sampler 2400 in accordance with aspects of the present disclosure. In this embodiment, a mobile frame 2402 for the aggregating sampler 2400 is shown as having an upper support 2416A and a lower support 2416B that are adjustable with respect to each other, such as adjustably coupled to a lower support 2416C. A plate 2440 is coupled to the upper support 2416A and extends between the upper support 2416A and the lower support 2416B. The plate 2440 is used to define a guide surface 2412 and a sample surface 2414 such that consumable product flows from the guide surface 2412 to the sample surface 2414. The height and angle of the guide surface 2412 and the sample surface 2414 may also be adjustable, such as by adjusting the height of the upper support 2416A and the lower support 2416B with respect to the lower support 2416C. A sampling sheet 2406 is removably secured to the sample surface 2414, such as through one or more fasteners 2408. The fasteners 2408, which are shown as clamps or pins, are secured to the edges of the sampling sheet 2406 and the sample surface 2414.

In one or more aspects, the center-of-gravity (COG) for the aggregating sampler may be lowered to facilitate use and stability within a sampling environment that includes a product stream. The COG may be lowered, for example, by using lower density materials, such as plastic or composite resin, for the guide surface, the cowling, and/or the sample surface. The size of the guide surface and the sample surface may also be reduced to lower the COG. Further, mass may be added to the lower end of the mobile frame, and/or an anchor point to the process line may be added to the mobile frame to provide stability to the aggregating sampler.

In one or more aspects described above, the aggregating sampler may use gravity to assist the flow of the consumable product through the aggregating sampler. Generally, the flow of the consumable product is lifted initially, such as at the beginning of a process stream, and then descend as moving from one operation to the next operation within the process stream. As the aggregating sampler may be included within the process stream, the aggregating sampler may include a lift mechanism or a lift conveyor to facilitate use within a processing environment. The consumable product can be lifted by a conveyor before sampling and/or after sampling, such as to convey the consumable product into a bin. The conveyor may include one or more different types of conveyor or conveyance systems, including, but not limited to conveyor belts, cleated conveyer belts, screw augers, Archimedes pump, chain conveyors, and/or various bucket systems. Further, power may be provided to the conveyor using a portable power source, such as through a battery, to increase the mobility of the aggregating sampler. Alternatively, the conveyor may use an external power source to power the conveyor.

Figure 25:
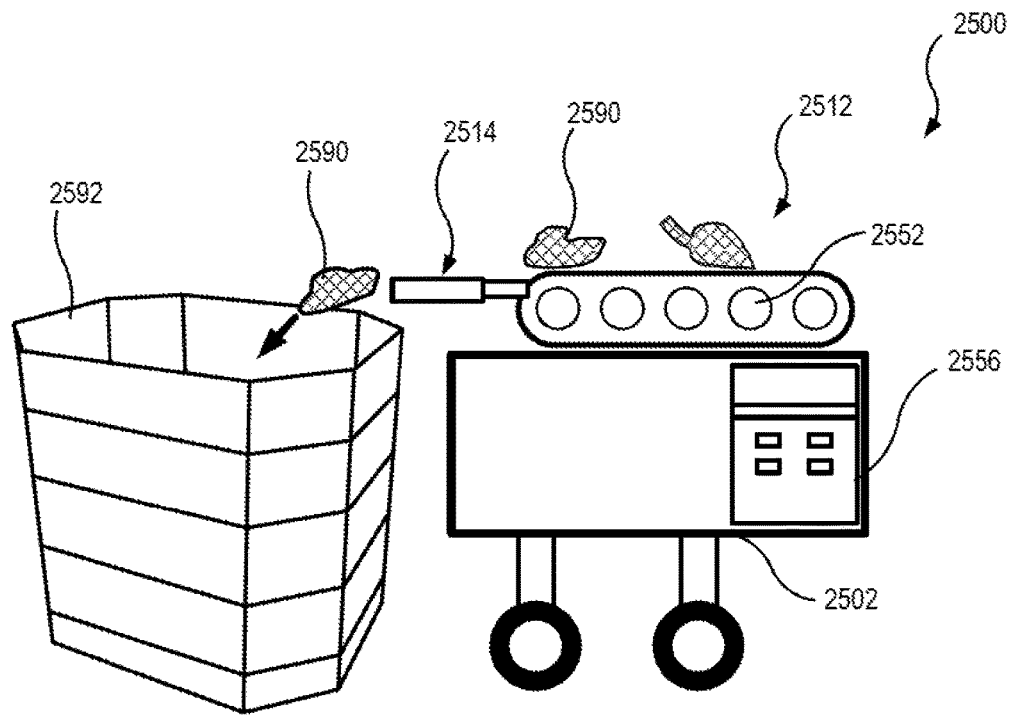
FIGS. 25 and 26 illustrate a mobile aggregating sampler that includes a conveyor in accordance with aspects of the present disclosure.
Figure 26:
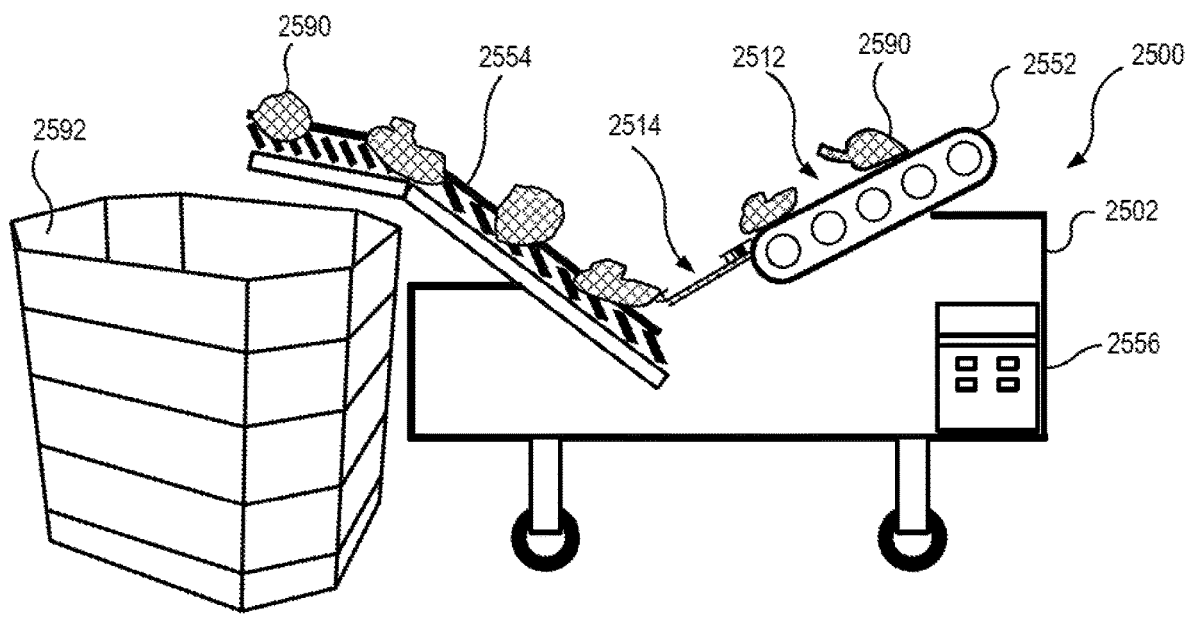

Accordingly, with reference to FIGS. 25 and 26, an aggregating sampler 2500 in accordance with aspects of the present disclosure may be powered and/or may include a conveyor to provide consumable products 2590 to a bin 2592. The aggregating sampler 2500 includes a mobile frame 2502 with a guide surface 2512 and a sample surface 2514. The guide surface 2512 in FIGS. 25 and 26 includes a guiding conveyor 2552 that moves with respect to the mobile frame 2502 to convey the consumable products 2590 from the guide surface 2512 to the sample surface 2514. The guiding conveyor 2552 is positioned substantially horizontal in FIG. 25, and is positioned at a non-horizontal angle in FIG. 26. The sample surface 2514 may be positioned at an angle with respect to the guiding conveyor 2552, or may be positioned at the same angle as the guiding conveyor 2552. Further, a controller 2556 may be included within the aggregating sampler 2500 and coupled to the mobile frame 2502, such as to control a speed, angle, and/or direction of the guide surface 2512 or guiding conveyor 2552. The controller 2556 may receive a user input to control one or more aspects of the aggregating sampler 2500 and/or may automatically control one or more aspects of the aggregating sampler 2500, such as through internal rules or inputs from one or more sensor sources or other inputs.

With reference to FIG. 26, the aggregating sampler 2500 may include a conveyor 2554 to convey the consumable products 2590 from the sample surface 2514 to the bin 2592. The conveyor 2554 is positioned adjacent the sample surface 2514 or downstream (with respect to the flow of the consumable products 2590 through the aggregating sampler 2500) the sample surface 2514 to receive the consumable products 2590 from the sample surface 2514. The conveyor 2554 then moves with respect to the mobile frame 2502 to convey the consumable products 2590 away from the sample surface 2514 and to the bin 2592. As shown, the conveyor 2554 may be used to convey the consumable products 2590 upward and to the bin 2592. Further, controls 2554 may be included with the aggregating sampler 2500 and coupled to the mobile frame 2502 to control the guiding conveyor 2552 and/or the conveyor 2554. FIGS. 27A-27D illustrate another embodiment of a mobile aggregating sampler 2700 in accordance with aspects of the invention.

Figure 27A:
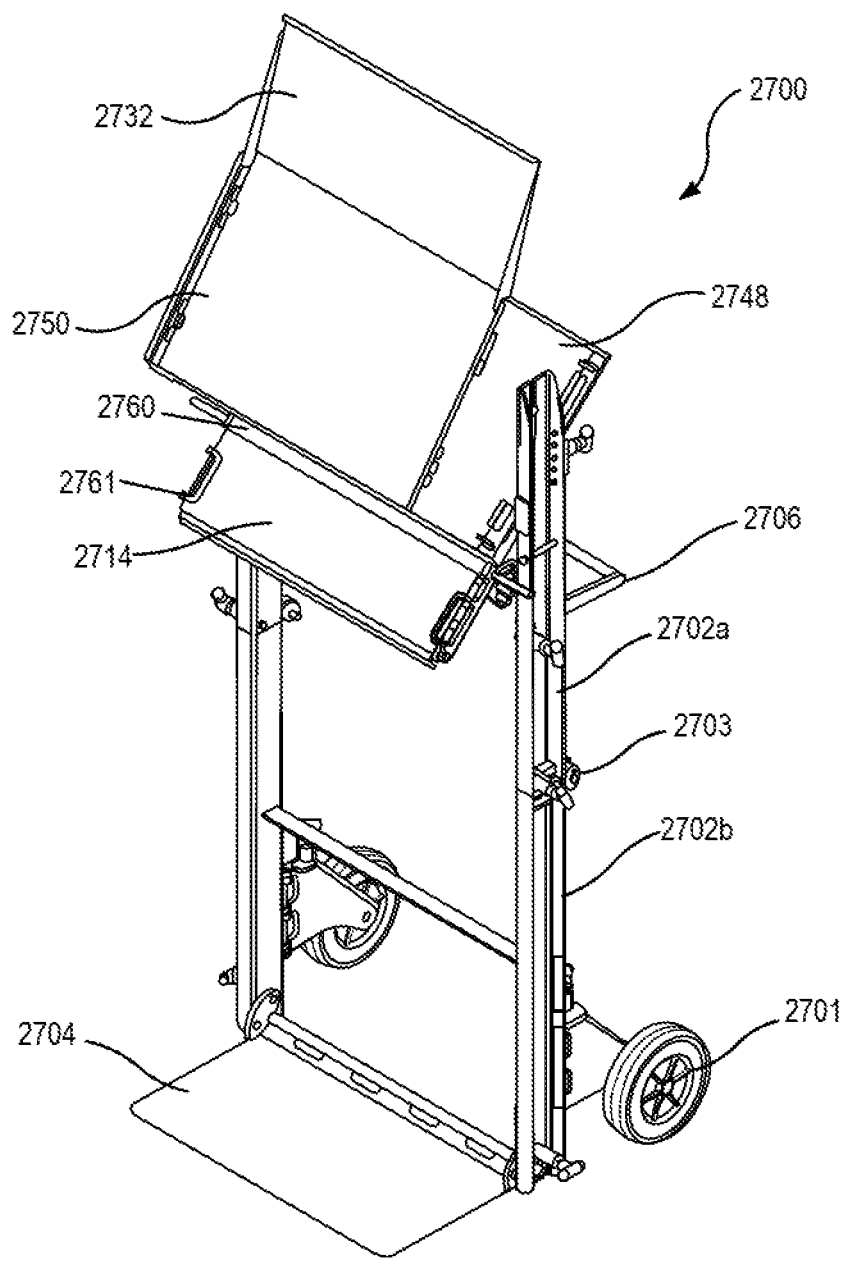
FIGS. 27A-27D illustrate a mobile aggregating sampler in accordance with aspects of the present disclosure.
Figure 27B:
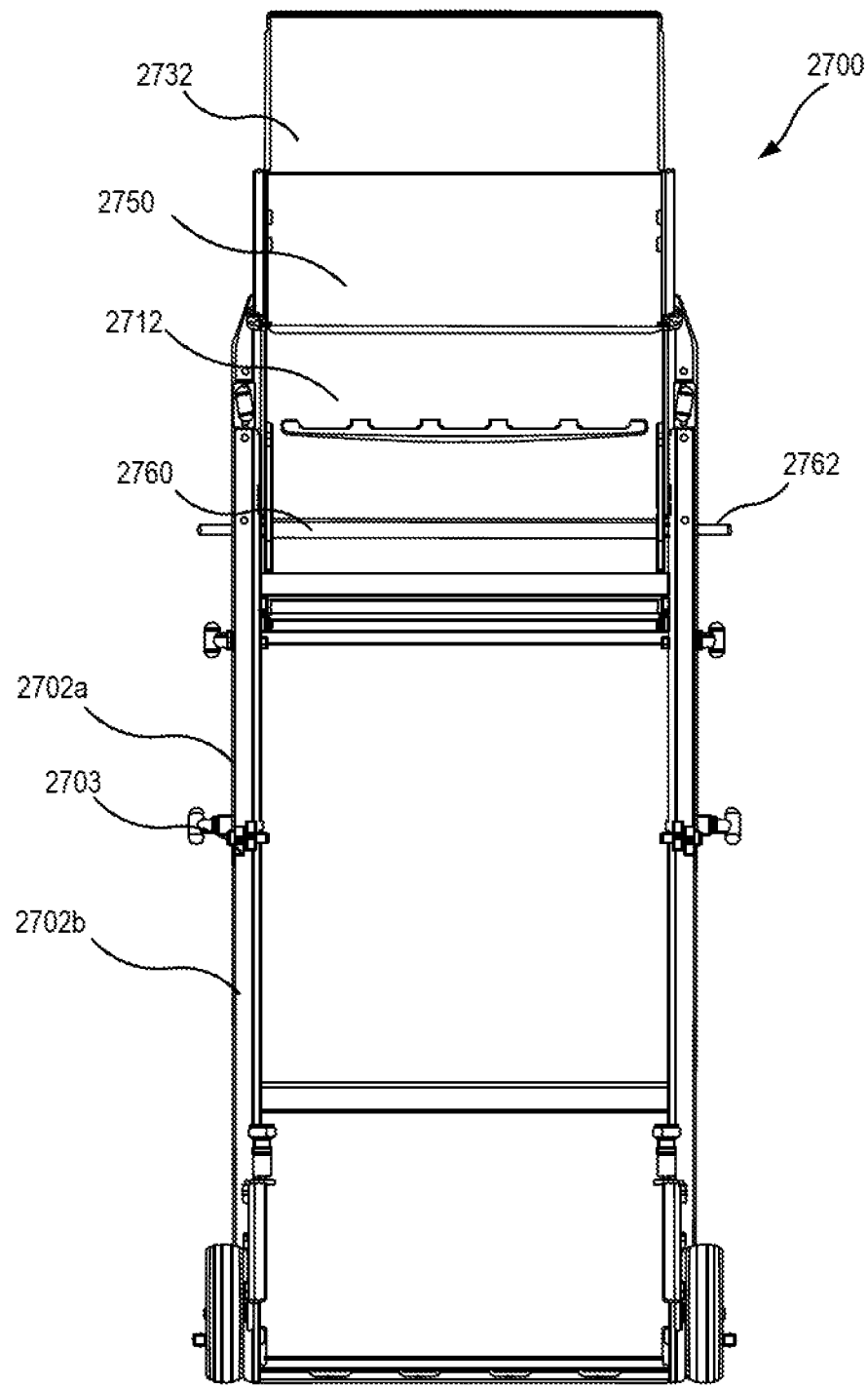
Figure 27C:
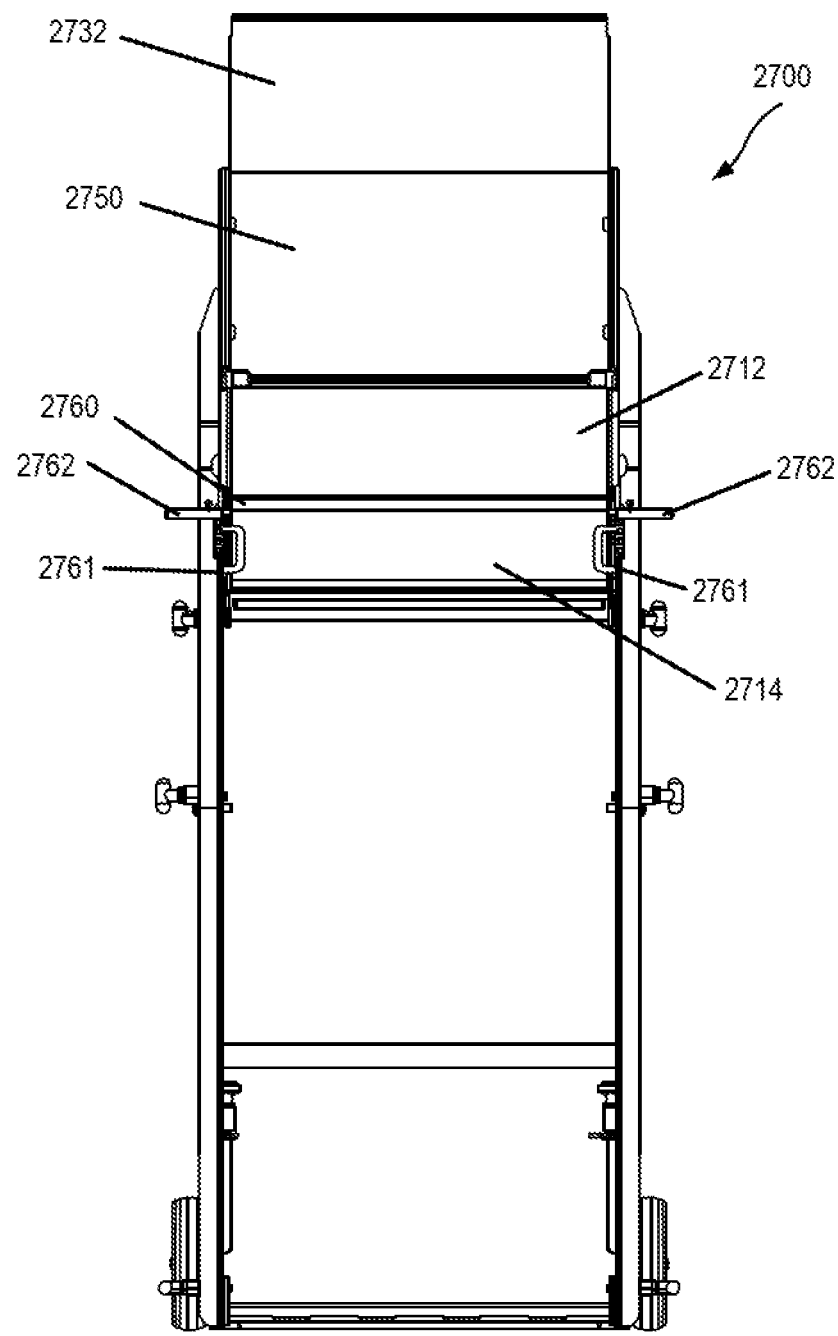
Figure 27D:
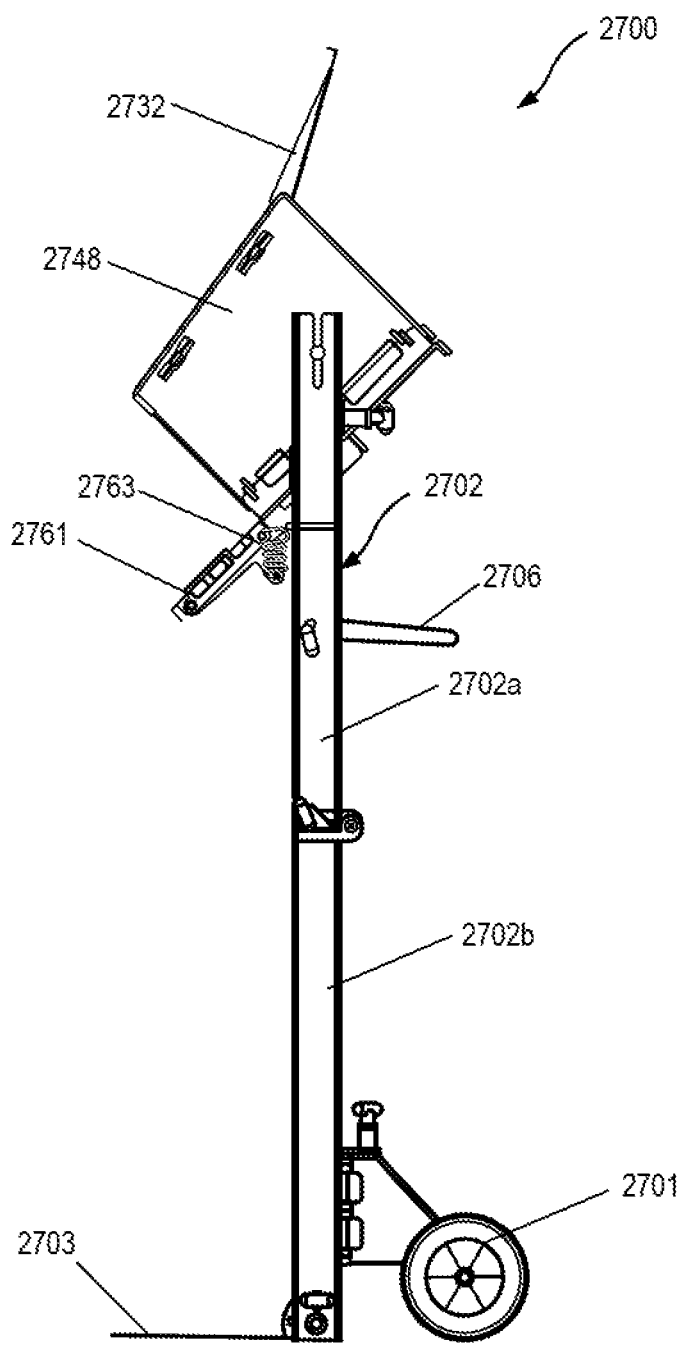

FIG. 27A is a front perspective view, FIG. 27B is a rear view, FIG. 27C is a front view, and FIG. 27D is a side view. Similar to the embodiment in FIG. 23A, the sampler 2700 includes a chute defined by a lower guide surface 2712, side guide surfaces 2748, an above guide surface 2750 with an optional cowling 2732 extending upwards along the inlet of the chute. The chute is typically set at an angle, for example about 45 degrees from horizontal as shown in FIG. 27D so that when placed distally of a conveyance system, conveyed items, such as food products, are directed through the chute. The sample surface 2714 (e.g. a cloth) is attached along a lower portion of the guide surface 2712 so that products directed through the chute along guide surface 2712 contact the sample surface 2714 before being collected. The chute is supported on a mobile frame 2702 having wheels 2701 that allow the sampler 2700 to be positioned at various locations, for example, moved between multiple conveyance systems. The mobile guide can further include a base plate 2703 along the floor. Typically, the conveyed products are collected in a collection bin resting atop base plate 2703, which allows the collection bin (not shown) to be easily moved after being filled with conveyed products. The mobile frame can further include a handle 2706 to facilitate manual transport and positioning of the mobile frame and subsequent movement of a filled collection bin. In some embodiments, the frame can include an extendable portion such that the chute can be raised to differing heights and fixed in place by a clamp or lock to allow the chute to be positioned to an appropriate height as needed for a particular conveyance system.

In the embodiment shown in FIG. 27A-27D, the guide surface 2712 of the chute extends further along the discharge direction than the side or top surfaces to allow for ready removal and replacement of the sampling surface 2714 disposed thereon. In addition, the chute is designed with a taper such that the intake has a greater height than the discharge so as to direct conveyed products received in the chute toward the sampling surface. In the embodiment shown, the intake clearance is about 13" and the discharge clearance is about 10". It is appreciated that this design could be configured according to various different shapes and sizes to accommodate a given conveyance system and with more or less of a taper, or without any taper.

In one aspect, the design in FIGS. 27A-27D provides a lighter weight design than previous embodiment as it includes thinner stainless steel for the beam and lower portions. Typically, the components of the chute are formed of stainless steel to allow for easy cleaning and sanitation.

In another aspect, this design includes an individual sampling surface holding mechanism for holding the sampling sheet (e.g. cloth) without need for a separate baseplate and cartridge. For example, as shown in FIGS. 27A-27D, the sampling surface 2714 is secured onto the discharge portion of the guide surface 2712 by a cross bar 2760 that holds the top surface taut against the guide surface 2712. The cross-bar 2760 extends between side brackets 2761 having inwardly extending portions that engage the sampling surface along each side, thereby holding the sampling surface in place without the need for a separate cassette or cartridge. While these inwardly extending portions of the side brackets 2761 are shown as looped portions, it is appreciated that the side brackets could be designed according to various differing shapes. The cross-bar can further include elongate posts 2762 that extend further beyond the sides of the mobile frame, the posts 2762 serve as handles for opening the sampling sheet holding device and are where the spring clips 2763 engage and pull the sampling sheet holder mechanism down to hold the sheets in place, as shown in FIG. 27D. The side brackets and cross-bar can be secured to the guide surface 2712 by interfacing features (e.g. pins/holes) and secured in place by any suitable fastening mechanism, such as the spring clip 2763 shown in FIG. 27D, which is attached to the frame to allow rotation to capture the pins or handles on 2760 assuring pressure on 2760 and 2761 on the sampling sheet. The attachment can be by pin, screw or other means that allows rotation to capture the handles. It is appreciated that the sampler 2700 can also be made compatible with a cartridge or cassette version mounted on a base plate.

In yet another aspect, this design is advantageous as it can be readily disassembled and folded for space saving purposes. For example, as shown in FIGS. 27A-27D, the mobile frame includes a top portion 2702a and a lower portion 2702b with a hinge 2703 in between such that the entire mobile frame can be folded upon removable of the spring latch pin next to the hinge to facilitate storage of the folded frame in a smaller place. Further, the chute and wheels can be disassembled by removal of any associated locks or fasteners, for example, the spring latch pins shown in FIGS. 27A-27C. The base plate 2703 can also be folded up and locked into place with the associated fastener and the handle 2706 can also be removed upo removal of its associated fastener. As shown in FIG. 27A, these associated fasteners are spring latch pins, although it is appreciated that any suitable fastener could be used.

While FIGS. 27A-27C show a particular design, it is appreciated that this design could be modified with various features added or removed and still be in accordance with the concepts of the invention described herein. For example, the sampler could include just the guide surface 2712 and sample surface 2714, or could include a partial chute with the guide surface 2712 and side guide surfaces 2714, or the cowling could be adjustable or omitted entirely.

Examples of Extraction

The reference method for extracting microorganisms from grab samples is homogenization by mixing or stomaching with an appropriate amount of fluid, usually a buffer. The purpose of adding fluid is to neutralize any antimicrobial or other properties of the sample that may be unfavorable for microbial growth such as low pH and suspend microorganism in liquid to facilitate downstream testing. However, adding fluid also dilutes the concentration of the microorganisms in the sample. Because most microbiological testing only take a portion of the homogenate (e.g., 0.1 mL or 1 mL for plating; 2.5 µL for direct PCR), the homogenization by dilution method decreases the detectability of the organisms of interest by as much as 1,500,000 times. To increase the detectability, a lengthy enrichment procedure is incorporated to allow a single viable cell to proliferate to millions so that it can be detected. This procedure costs 24 to 48 hours delay in obtaining detection data and more days in decision making time due to subsequent confirmation steps. It is also important that the samples be preserved properly and extraction be done as close to sampling time as possible. If the sample has changed before extraction, the results do not represent the tested lot.

For most conventional sampling programs, the percentage of negative samples exceeds 99%. Based on simple modeling, one can easily conclude that the number of cells of the organism of interest is seldom more than 1 and probably rarely more than 5 based on a Poisson distribution. With so few cells present, the enrichment is often done in the extraction buffer. This is critical with the small sampling but does not make this type of testing any more representative of the lot under test.

When extracting the sampling materials these same considerations apply. However, the impact on the results of failing to extract one organism is an order of magnitude or smaller due to the larger effective sample. In addition, the cassettes afford the opportunity to begin the extraction faster by adding the fluid immediately after sampling providing maximal time for the extraction to occur while avoiding human interaction.

Examples of Concentration

During the concentration, two classes of materials may need to be removed, the small, <100,000 molecular weight, and the very large, >50 microns. In addition, the sample may need to be concentrated to about 1 mL to be compatible with the screening detection system. Given that the extraction generally starts at about 200 mL, there is a large amount of water to remove.

Two schemes are practical. Traditionally, one can filter the extraction fluid through an inert 50 microns cut off filter and then sediment the organisms of interest by centrifugation. The resulting pellets can be re-suspended in an appropriate buffer and taken on to cleaning. Alternatively, after filtration, the small molecules and water can be removed osmotically with adsorbents or pressure and a semi-permeable membrane such as used for reverse osmosis or ultrafiltration. The latter is more amenable to automation as the resultant concentrated sample remains in solution. However, this option may require a for purpose module to be executed.

It is important to maintain the connection to the initial Meta data through this process. If enough of interfering material is removed and the sample is sufficiently concentrated, the cleaning step examined next can be skipped and moving directly to the screening determination. This decision determination may be made of a case by case basis.

Examples of Cleaning

At this point in the process, samples have been greatly reduced in volume but the organisms of interest have not been segregated from other organism so the signal to noise ratio is till problematic. In addition, further concentration may be needed for detection without enrichment during which one organism is converted to many at the cost of time and delay in decision making.

Several schemes are practical but all involve binding the organisms of interest in a small area such as a microfluidized or nanofluidized channel. This channel or area may or may not be filled with surface activated nanofiber. Utilizing elasto-inertial microfluidics, the viscoelastic flow enables size based migration of larger particles into a non-Newtonian solution, while smaller bacteria remain in the streamline of the blood sample entrance and can be separated. It is tempting to consider surface activated magnetic particles; however, the mechanical manipulation of these particles to achieve the desired small volume is a larger engineering challenge than activating the small surface area. However, any binding geometry that fixes the organisms of interest and any other organisms selected to represent the other microflora in an appropriate small volume can be used.

The surface activation may require numerous active binding sites in close proximity. The mixed DNA primer arrays of SnapDNA are one class of materials. Another class is a cocktail of antibodies for all the organisms of interest.

The binding mechanism may bind all the organism of interest. These organisms may be sufficiently bound that other organisms and materials are selectively removed from the area of binding as clean fluid is passed through the channel.

The motive force to move the cells through the channel can be the mechanical action of fluid flow, electrostatic as the surface of most bacteria is negative, or a size pumping action such as practiced with ferromagnetic particles.

Examples of Screening Detection

With the partially purified organism or organisms of interest bound in a small area or small volume if the cleaning step proves unnecessary, many approaches are available for screening detection for process control. The functional requirements are clearer. First and foremost is that enrichment culture takes substantial amounts of time, and such should be eliminated or reduced in one or more cases. Second, the screening metric may need to be an index suitable for statistical process control. This implies a measurement with many states as opposed to binary 0 and 1. The magnitude of this metric may relate to the extent of deviation from normal operation and therefore the likelihood that an outbreak could occur. Under these conditions, the detection of deviation can be based on the classic rules for control charting. Furthermore, trend detecting rules have the potential to detect problems before significant deviations have occurred. The statistically based Westcard rules provide one basis for trend analysis.

Expressed differently, an index may be needed that tallies the relative presence of beneficial organisms and potential pathogens and aggregates this information in a useful way. As more information is acquired about specific products, the power of big data will come into play. However, at the simplest levels, the aggregate level of potential pathogen is a useful screening tool. The relative balance between potential pathogens and beneficial organisms is a more sophisticated analysis to compensate for seasonal variations that are inherent in many products. It is reasonable to expect to develop indices that are product specific.

The information behind indices is evolving rapidly. The simplest useful index is a ratio of pathogen intensity to a benign organism. These can be generated by many means including classical enumeration with plating, but the classical methods are two slow to meet the functional requirements outlined above. However, given the concentration of the organisms on the cleaning substrate or the concentrated extraction, it is possible to go directly to qPCR in some cases to generate index data.

There are two schemes for generating this type of data at its most sophisticated level. First, one can use a collection of ligands (antibodies, aptamers, or others) that bind and tag all the organisms of potential interest yielding a collection of signals that are multiplexed into a family of useful channels. Alternatively, one can generate an array of specific binding interactions that are analyzed chemometrically to yield a metric. The latter approach will be faster and probably less expensive after the research and analysis is done.

As an example of the first scheme would be a using a mixture of conjugated antibodies to bind to all types of cells of interest. For produce, hemolytic *E. coli, Salmonella* and *Listeria* are of greatest interest. Poultry focuses on *Campylobacter* and *Salmonella*. Other industries have other and additional interests. These antibodies can be bound to the organisms bound to the cleaning substrate. The retained tags with either a fluorescent probe or an enzyme provide signal amplification and detection. When the cleaning region as a small enough cross section, the signal from the hundreds to thousands of cells on the cleaning substrate are detectable. Micro and nano fluidization are necessary. However, specific detection protocols can be evaluated at a macro scale using an appropriately instrumented microscope that can be used to measure the signal from a small area where cells have been collected. For speed to market, multiple detectors can be run in parallel or series to generate similar multiple channels of data.

The alternative scheme invokes the lab on a chip concept. By building an array of binding sites, the composition of the samples can be queried. PCR can amplify the contents selectively with a collection of primers. Such detectors can evolve to providing both the screening detection of this step and the ultimate secondary screening. However, it is likely to remain a two-step process due to the economics.

A number of technologies can meet these requirements including but not limited to, for example: 1) Sensors where the vibrational frequencies (which may for example include optical waveguide), impedance, or other properties of a transistor are modified by the binding of the organisms of interest to the sensor. This approach may require that the sensor be built into the surface of the channel. Another technology may include, 2) qPCR where the cells are laid in place and the number of copies of the organisms of interest, or the number of ribosomes of the organisms of interest are estimated. Another technology may include, 3) Use tagged antibodies to light up the organisms of interest so that they can detected on the absorbent surface spectrophotometrically. Enzyme, fluorescent probes, and other materials to amplify the signal can be used.

It may be desirable to avoid confirmation of the presence of one or more specific pathogens during this screening. This is where the trade between LOD and speed to useful information. If the signal is not about three times background, no further action is warranted.

Examples of Confirmation

The confirmation step will be applied when there is reason to suspect that a pathogen is present. The technology in this area is evolving rapidly with many new approaches and efficiencies being developed and introduced. Some will use the techniques suggested for screening with more specific reagents for the confirmation. At present, all the common procedures rely on either molecular biology or ligand binding reactions. Various strategies have been developed to amplify the signal noise ratio and to identify the contaminant to the desired specificity. The desired specificity ranges from simple speciation to identify specific serotypes.

For confirmation, a concentrated sample such as afforded the screening detection above may be included. The concentration may be included due to the small volumes that are compatible with these types of procedures. The organisms, the surface antigens from the organisms, or the nucleic acid from the organisms may need to be extracted from the screening system to the extent that these materials can interact with the reagents of the confirmation procedure. In other words, there is not a priory reason that the detection module could not be engineered for a second round of chemistries. Any one of these materials may contain the information necessary to characterize the contaminant. There are a number of these processes and they are being improved. The choice of approach will be driven by cost, desired specificity and the desired speed.

Many strategies are available to amplify the base signal from these materials that will still be present at only modest concentration in the typical sample. The yield of material from the hundreds to thousands of organisms of interest bound to the screening detector platform is still very small. Amplification based on radio isotopes are largely out of favor but still possible. However, enzyme systems are still in use and new enzymes strategies are still being developed such as those used for ELISA methods or with a luciferase. Fluorescent tags on specific antibodies such as those proposed for the screening determination are less useful for this purpose due the high potential for cross reactivity. However, antibodies of this type are the basis for the serotyping classifications that up until recently has been the standard for characterization. These older serotyping assays may require isolation and growing the organisms.

Increasingly characterization is based on the presence of sequences of nucleic acid. These can be nuclear DNA, ribosomal RNA, or messenger RNA. At the extreme, it is now practical to sequence the entire genome of the organism. Increasing specificity is useful for identification of the source a contamination. However, it also presents a potential liability in the case of an outbreak of illness.

The molecular assays are built around the use of enzymes to replicate sequences of nucleic acid to generate a large enough signal for detection. Various primers are used to select which portions are copied; up to and including the entire genome. For measurement, various fluorescent tags are used. One of the newest techniques utilizes the melting and binding of target material to known sequences to generate a complex matrix of information that can be used chemometrically in lieu of complete sequence data.

Examples of Reporting and Roll Up

Both the screening detection and the confirmation results are reported directly to a sequel database. This reporting may not require human intervention if the included quality assurance standards (positive and negative controls) fall within normal ranges. This avoids transcription and transposition errors. Digital records are more reliable and accurate than manual records.

Both detectors should be part of the "Internet of Things". This connectivity allows results to be pushed to operators on the floor allowing for the rapid release of product or for the redisposition of product if a potential issue is identified that may need to be addressed. Once the results are in an appropriate database, various users can have customized interfaces providing the information. Some may need to track individual results. Others may be more interested in trends and averages. There may be provided a class of users that may want to aggregate even larger data sets to compare across locations.

There are many platforms available for extracting information from the database. For example, but not limited thereto, Ignition has proven useful in this record as it is open source allowing customization.

In accordance with an aspect of the disclosure, a method for microbial sampling food may include gathering a microbial sampling from one or more food items, extracting microorganisms from the microbial sampling, concentrating the microorganisms, cleaning the microorganisms, tallying a relative presence of the microorganisms and any potential pathogens, aggregating information of the microorganism tally into a microorganism report, confirming the microorganism tally, and reporting the microorganism report of the microorganism tally.

In some cases, gathering the microbial sampling from the one or more food items includes sampling, using an aggregating sampler, the one or more food items that include a production lot of produce or meat creating one or more samples that makes up the microbial sampling. Rhe one or more samples may be configured to be processed to indicate if pathogens are present at no greater than a normal background.

In some cases, the method may further include assessing, using an aggregating sampler, a level of cross contamination control to validate or verify a wash process. Gathering the microbial sampling from the one or more food items may include providing an aggregating sampler at a sampling location. The sampling location may be at least one of in a field, at harvest, just after dumping or cutting, in a wash system, or after the wash system.

In some cases extracting includes enriching the microbial sampling, and adding fluid to the microbial sample. In some cases concentrating includes filtering extraction fluid of the microbial sampling using at least one of centrifugation filtering or osmotically filtering. In some cases, cleaning includes binding the microorganisms in a small area including one or more of a microfluidized or nanofluidized channel. In some cases tallying includes using a collection of ligands that bind and tag all the organisms of potential interest yielding a collection of signals that are multiplexed into a family of useful channels. In some cases ligands include one or more of antibodies, primers, and aptamers.

In some cases tallying includes generating an array of specific binding interactions that are analyzed chemometrically to yield a metric. The method may further include building an array of binding sites, wherein the composition of the samples can be queried, and amplifying, using a PCR, the contents selectively with a collection of primers.

In some cases confirming includes extracting surface antigens from the organisms or nucleic acid from the organisms from a screening system to the extent that these materials can interact with the reagents of a confirmation procedure. In some cases confirming further includes amplifying a base signal of the microorganism tally.

In some cases, the method may further include use of an index as a surrogate for direct results regarding presence or absence of organisms of interest. In some cases, the method may further include use of a statistical process control for detecting deviations in microbial flora.

In accordance with an aspect of the disclosure, a method of applying aggregating sampling to food items including providing at least one aggregating sampler at one or more sampling locations, and sampling, using the at least one aggregating sampler, a production lot of produce or meat creating one or more samples that makes up a microbial sampling.

In some cases the one or more samples are configured to be processed to indicate if pathogens are present at no greater than a normal background. In some cases, the one or more sampling locations includes at least one of in a field, at harvest, just after dumping or cutting, in a wash system, or after the wash system. The method may further include assessing, using the aggregating sampler, a level of cross contamination control to validate or verify a wash process.

In accordance with an aspect of the disclosure, an apparatus for microbial sampling, including means for gathering a microbial sampling from one or more food items, means for extracting microorganisms from the microbial sampling, and means for concentrating the microorganisms, means for cleaning the microorganisms, means for tallying a relative presence of the microorganisms and any potential pathogens, means for aggregating information of the microorganism tally into a microorganism report, means for confirming the microorganism tally, and means for reporting the microorganism report of the microorganism tally.

In accordance with an aspect of the disclosure, an apparatus for microbial sampling, includes at least one processor configured to generate control signals for controlling gathering a microbial sampling from one or more food items, extracting microorganisms from the microbial sampling, concentrating the microorganisms, cleaning the microorganisms, tallying a relative presence of the microorganisms and any potential pathogens, aggregating information of the microorganism tally into a microorganism report, and confirming the microorganism tally, and a transmitter configured to transmit the microorganism report of the microorganism tally. In some cases the apparatus may further include an aggregating sampler configured to gather the microbial sampling.

In accordance with an aspect of the disclosure, a non-transitory computer readable medium for microbial sampling having instructions stored thereon for gathering a microbial sampling from one or more food items, extracting microorganisms from the microbial sampling, concentrating the microorganisms, cleaning the microorganisms, tallying a relative presence of the microorganisms and any potential pathogens, aggregating information of the microorganism tally into a microorganism report, confirming the microorganism tally, and reporting the microorganism report of the microorganism tally.

In accordance with an aspect of the disclosure, a method for sampling food including concentrating microorganisms and removing interference, tallying a relative presence of the microorganisms and any potential pathogens, and aggregating information of the microorganism tally into a microorganism report. In accordance with an aspect of the disclosure, a system capable of implementing one or more of the novel aspects discussed in this application disclosure.

In accordance with an aspect of the disclosure, a microbial aggregating sampler, including a covering including a microbial sampling material with a pocket formed in the covering to receive an appendage or a tool for handling of the covering.

In some cases, the covering includes an attachment feature formed in the pocket to receive the tool. In some cases, the attachment feature includes one of a hole formed through the covering, a loop positioned within the pocket to receive an end of the tool there through, and a tab positioned within the pocket for an end of the tool to attach thereto.

In some cases the covering includes a sheath formed in the pocket to receive a digit of an appendage. In some cases the pocket is formed through the covering such that the appendage or the tool for handling the covering extends through the covering. In some cases the covering is completely formed from the microbial sampling material. In some cases the covering includes two sheets attached to each other to form the pocket. In some cases the covering includes a single sheet folded and attached to itself to form the pocket.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c). As used herein, including in the claims, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." For example, the articles "a" and "an" as used in this application and the appended claims should generally be construed to mean "one or more" unless specified otherwise or clear from the context to be directed to a singular form. Unless specifically stated otherwise, the term "some" refers to one or more. Moreover, the term "or" is intended to mean an inclusive "or" rather than an exclusive "or." That is, unless specified otherwise or clear from the context, the phrase, for example, "X employs A or B" is intended to mean any of the natural inclusive permutations. That is, for example the phrase "X employs A or B" is satisfied by any of the following instances: X employs A; X employs B; or X employs both A and B. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

If implemented in hardware, an example hardware configuration may comprise a processing system in a wireless node. The processing system may be implemented with bus architecture. The bus may include any number of interconnecting buses and bridges depending on the specific application of the processing system and the overall design constraints. The bus may link together various circuits including a processor, machine-readable media, and a bus interface. The bus interface may be used to connect a network adapter, among other things, to the processing system via the bus. The network adapter may be used to implement the signal processing functions of the PHY layer. In the case of a user terminal 120 (see FIG. 1); a user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer readable medium. Software shall be construed broadly to mean instructions, data, or any combination thereof, whether referred to as software, firmware, middleware, microcode, hardware description language, or otherwise. Computer-readable media include both computer storage media and communication media including any medium that facilitates transfer of a computer program from one place to another. The processor may be responsible for managing the bus and general processing, including the execution of software modules stored on the machine-readable storage media. A computer-readable storage medium may be coupled to a processor such that the processor can read information from, and write information to, the storage medium. In the alternative, the storage medium may be integral to the processor. By way of example, the machine-readable media may include a transmission line, a carrier wave modulated by data, and/or a computer readable storage medium with instructions stored thereon separate from the wireless node, all of which may be accessed by the processor through the bus interface. Alternatively, or in addition, the machine-readable media, or any portion thereof, may be integrated into the processor, such as the case may be with cache and/or general register files. Examples of machine-readable storage media may include, by way of example, RAM (Random Access Memory), flash memory, phase change memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module below, it will be understood that such functionality is implemented by the processor when executing instructions from that software module.

Also, any connection is properly termed a computer-readable medium. For example, if the software is transmitted from a website, server, or other remote source using a coaxial cable, fiber optic cable, twisted pair, digital subscriber line (DSL), or wireless technologies such as infrared (IR), radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk, and Blu-ray® disc where disks usually reproduce data magnetically, while discs reproduce data optically with lasers. Thus, in some aspects computer-readable media may comprise non-transitory computer-readable media (e.g., tangible media). In addition, for other aspects computer-readable media may comprise transitory computer-readable media (e.g., a signal). Combinations of the above should also be included within the scope of computer-readable media.

Thus, certain aspects may comprise a computer program product for performing the operations presented herein. For example, such a computer program product may comprise a computer-readable medium having instructions stored (and/or encoded) thereon, the instructions being executable by one or more processors to perform the operations described herein. For example, instructions for performing the operations described herein and illustrated in the appended figures.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

What is claimed is:

1. An aggregating sampler for microbial sampling of consumable products, the sampler comprising:
    a mobile frame comprising an upper end and a lower end;
    a guide coupled to the mobile frame and having a guide surface positioned such that the consumable products received upon the guide surface pass along the guide surface;
    a side guide surface positioned adjacent the guide surface and extending upward from the guide surface; and
    one or more sample sheets coupled to the guide and/or mobile frame and positioned along or adjacent a lower portion of the guide surface and extending along a first plane disposed at an angle between 1 degree and 89 degrees relative a horizontal plane such that the consumable products received from the guide surface pass along a sample surface of the sample sheet positioned along or adjacent the lower portion of the guide surface, wherein the sample sheet comprises a microbial sampling material to contact the consumable products that pass along the sample surface.

2. The sampler of claim 1, wherein the guide surface is positioned coplanar with the first plane.

3. The sampler of claim 2, wherein the angle of the first plane along which the guide surface or the sample surface extends is configured to be adjusted with respect to the horizontal plane.

4. The sampler of claim 1, wherein the angle of the guide surface or the sample surface is between 30 degrees and 60 degrees with respect to the horizontal plane.

5. The sampler of claim 4, wherein the angle of the guide surface or the sample surface is at 45 degrees with respect to the horizontal plane.

6. The sampler of claim 1, wherein the mobile frame comprises one or more wheels or one or more pads coupled to the lower end.

7. The sampler of claim 1, wherein a height of the guide surface and the sample surface is adjustable with respect to the lower end of the mobile frame.

8. The sampler of claim 1, wherein the mobile frame, the sample surface, and the guide surface comprise a food contact material identified under 21 Code of Federal Legislation (C.F.R.) §§ 170-190.

9. The sampler of claim 1, further comprising a fastener securing the one or more sampling sheets to the sample surface.

10. The sampler of claim 1, wherein the guide surface or the sample surface is coupled to the mobile frame.

11. The sampler of claim 10, wherein the sample surface comprises a cartridge such that the one or more sampling sheets are removably secured within the cartridge.

12. The sampler of claim 11, wherein the cartridge comprises:
    a body;
    a cover movable with respect to the body with the one or more sampling sheets configured to be positioned between the cover and the body; and
    a fastener to removably secure the cover to the body.

13. The sampler of claim 1, wherein the sample surface comprises a sampling conveyor that is configured to move with respect to the mobile frame.

14. The sampler of claim 13, wherein the sampling conveyor comprises a rotating assembly that is configured to rotate with respect to the mobile frame.

15. The sampler of claim 13, wherein the sampling conveyor is configured to translate with respect to the mobile frame.

16. The sampler of claim 1, wherein the one or more sampling sheets is configured to move with respect to the mobile frame or the sample surface.

17. The sampler of claim 16, wherein the one or more sampling sheets comprises a roll of microbial sampling material that is configured to rotate about an axis substantially parallel or perpendicular to a flow path of the consumable products along the guide surface.

18. The sampler of claim 1, wherein the guide surface comprises a guiding conveyor configured to move with respect to the mobile frame to convey the consumable products from the guide surface to the sample surface.

19. The sampler of claim 1, wherein the one or more sampling sheets are attached by a cross-bar extending across the guide surface to engage an upper edge of the exposed sampling sheet and by side portions extending along each opposite side of the exposed sampling sheet.

20. The sampler of claim 19, wherein the side portions comprise side brackets that attach to sides of the guide by interfacing features and are secured by one or more fasteners on each side.

21. A method of aggregate sampling items, the method comprising:
   positioning an aggregate sampler as in claim 1 at a discharge of a conveyance system;
   attaching the sampling sheet to the guide and/or the mobile frame;
   conveying items with the conveyance system so that a plurality of items contact the sampling sheet after discharge from the conveyance system;
   removing the sampling sheet after the items are conveyed; and
   testing the sampling sheet and associating a result with the items conveyed.

22. An aggregating sampler for microbial sampling of consumable products, the sampler comprising:
   a mobile frame comprising an upper end and a lower end;
   a guide coupled to the mobile frame and having a guide surface positioned such that the consumable products received upon the guide surface pass along the guide surface, wherein the guide surface or the sample surface is coupled to the mobile frame;
   one or more sample sheets coupled to the guide and/or mobile frame and positioned along or adjacent a lower portion of the guide surface and extending along a first plane disposed at an angle between 1 degree and 89 degrees relative a horizontal plane such that the consumable products received from the guide surface pass along a sample surface of the sample sheet positioned along or adjacent the lower portion of the guide surface, wherein the sample sheet comprises a microbial sampling material to contact the consumable products that pass along the sample surface, wherein the sample surface comprises a cartridge such that the one or more sampling sheets are removably secured within the cartridge; and
   a cartridge holder removably coupled to the mobile frame and configured to removably receive a plurality of cartridges therein.

23. An aggregating sampler for microbial sampling of consumable products, the sampler comprising:
   a mobile frame comprising an upper end and a lower end;
   a guide coupled to the mobile frame and having a guide surface positioned such that the consumable products received upon the guide surface pass along the guide surface;
   one or more sample sheets coupled to the guide and/or mobile frame and positioned along or adjacent a lower portion of the guide surface and extending along a first plane disposed at an angle between 1 degree and 89 degrees relative a horizontal plane such that the consumable products received from the guide surface pass along a sample surface of the sample sheet positioned along or adjacent the lower portion of the guide surface, wherein the sample sheet comprises a microbial sampling material to contact the consumable products that pass along the sample surface; and
   a cowling coupled to the mobile frame and positioned above the guide surface or the sample surface such that the consumable products contacted by the cowling are routed to the guide surface or the sample surface.

24. An aggregating sampler for microbial sampling of consumable products, the sampler comprising:
   a mobile frame comprising an upper end and a lower end;
   a guide coupled to the mobile frame and having a guide surface positioned such that the consumable products received upon the guide surface pass along the guide surface;
   one or more sample sheets coupled to the guide and/or mobile frame and positioned along or adjacent a lower portion of the guide surface and extending along a first plane disposed at an angle between 1 degree and 89 degrees relative a horizontal plane such that the consumable products received from the guide surface pass along a sample surface of the sample sheet positioned along or adjacent the lower portion of the guide surface, wherein the sample sheet comprises a microbial sampling material to contact the consumable products that pass along the sample surface; and
   a bin support coupled to the mobile frame, positioned below the sample surface, and configured to receive a bin such that the consumable products pass along the sample surface and into the bin supported by the bin support.

25. An aggregating sampler for microbial sampling of consumable products, the sampler comprising:
   a mobile frame comprising an upper end and a lower end;
   a guide coupled to the mobile frame and having a guide surface positioned such that the consumable products received upon the guide surface pass along the guide surface;
   one or more sample sheets coupled to the guide and/or mobile frame and positioned along or adjacent a lower portion of the guide surface and extending along a first plane disposed at an angle between 1 degree and 89 degrees relative a horizontal plane such that the consumable products received from the guide surface pass along a sample surface of the sample sheet positioned along or adjacent the lower portion of the guide surface, wherein the sample sheet comprises a microbial sampling material to contact the consumable products that pass along the sample surface, wherein the sample surface comprises a sampling conveyor that is configured to move with respect to the mobile frame, wherein the one or more sampling sheets comprises a plurality of sampling sheets that are each removably secured to the sampling conveyor.

26. An aggregating sampler for microbial sampling of consumable products, the sampler comprising:

a mobile frame comprising an upper end and a lower end; and a guide coupled to the mobile frame and having a guide surface positioned such that the consumable products received upon the guide surface pass along the guide surface;

one or more sample sheets coupled to the guide and/or mobile frame and positioned along or adjacent a lower portion of the guide surface and extending along a first plane disposed at an angle between 1 degree and 89 degrees relative a horizontal plane such that the consumable products received from the guide surface pass along a sample surface of the sample sheet positioned along or adjacent the lower portion of the guide surface, wherein the sample sheet comprises a microbial sampling material to contact the consumable products that pass along the sample surface, wherein the one or more sampling sheets comprises a roll of microbial sampling material that is configured to rotate about an axis substantially parallel or perpendicular to a flow path of the consumable products along the guide surface, wherein the one or more sampling sheets is configured to move with respect to the mobile frame or the sample surface, wherein the roll is positioned within a roll housing configured to dispense the roll therefrom, and/or wherein the roll further comprises perforations formed therein and configured for a roll dispenser to engage the perforations when dispensing the roll.

27. An aggregating sampler for microbial sampling of consumable products, the sampler comprising:

a mobile frame comprising an upper end and a lower end;

a guide coupled to the mobile frame and having a guide surface positioned such that the consumable products received upon the guide surface pass along the guide surface;

one or more sample sheets coupled to the guide and/or mobile frame and positioned along or adjacent a lower portion of the guide surface and extending along a first plane disposed at an angle between 1 degree and 89 degrees relative a horizontal plane such that the consumable products received from the guide surface pass along a sample surface of the sample sheet positioned along or adjacent the lower portion of the guide surface, wherein the sample sheet comprises a microbial sampling material to contact the consumable products that pass along the sample surface; and a convey surface positioned adjacent the sample surface and configured to move with respect to the mobile frame such that the consumable products received upon the convey surface are conveyed away from the sample surface.

28. An aggregating sampler for microbial sampling of consumable products, the sampler comprising:

a mobile frame comprising an upper end and a lower end;

a guide coupled to the mobile frame and having a guide surface positioned such that the consumable products received upon the guide surface pass along the guide surface; and one or more sample sheets coupled to the guide and/or mobile frame and positioned along or adjacent a lower portion of the guide surface and extending along a first plane disposed at an angle between 1 degree and 89 degrees relative a horizontal plane such that the consumable products received from the guide surface pass along a sample surface of the sample sheet positioned along or adjacent the lower portion of the guide surface, wherein the sample sheet comprises a microbial sampling material to contact the consumable products that pass along the sample surface, wherein the sampler includes a chute, the lower inside surface of which is the guide surface.

29. The sampler of claim 28, wherein the chute is tapered such that an intake has a larger inside height than within an inside height of a discharge of the chute, the chute is readily removable by a user and/or the angle of the chute is readily adjustable.

30. An aggregating sampler for microbial sampling of consumable products, the sampler comprising:

a mobile frame comprising an upper end and a lower end;

a guide coupled to the mobile frame and having a guide surface positioned such that the consumable products received upon the guide surface pass along the guide surface; and one or more sample sheets coupled to the guide and/or mobile frame and positioned along or adjacent a lower portion of the guide surface and extending along a first plane disposed at an angle between 1 degree and 89 degrees relative a horizontal plane such that the consumable products received from the guide surface pass along a sample surface of the sample sheet positioned along or adjacent the lower portion of the guide surface, wherein the sample sheet comprises a microbial sampling material to contact the consumable products that pass along the sample surface, wherein the mobile frame is foldable to facilitate storage.

31. An aggregating sampler for microbial sampling of consumable products, the sampler comprising:

a mobile frame comprising an upper end and a lower end;

a guide coupled to the mobile frame and having a guide surface positioned such that the consumable products received upon the guide surface pass along the guide surface;

one or more sample sheets coupled to the guide and/or mobile frame and positioned along or adjacent a lower portion of the guide surface and extending along a first plane disposed at an angle between 1 degree and 89 degrees relative a horizontal plane such that the consumable products received from the guide surface pass along a sample surface of the sample sheet positioned along or adjacent the lower portion of the guide surface, wherein the sample sheet comprises a microbial sampling material to contact the consumable products that pass along the sample surface; and a chute, the lower inside surface of which is the guide surface, wherein the one or more sampling sheets are attached to a discharge portion of the guide surface that extends distally of the chute.

* * * * *